US012454510B2

(12) United States Patent
Zhang et al.

(10) Patent No.: US 12,454,510 B2
(45) Date of Patent: Oct. 28, 2025

(54) ISOPHTHALAMIDE COMPOUND AND USE THEREOF

(71) Applicant: METISA BIOTECHNOLOGY CO., LTD, Nanning (CN)

(72) Inventors: Lixin Zhang, Shenyang (CN); Jing Zhang, Shenyang (CN); Hongyan Pei, Shenyang (CN); Jie Wang, Shenyang (CN); Zhubo Sheng, Shenyang (CN); Zhuo Kang, Shenyang (CN)

(73) Assignee: METISA BIOTECHNOLOGY CO., LTD, Nanning (CN)

( * ) Notice: Subject to any disclaimer, the term of this patent is extended or adjusted under 35 U.S.C. 154(b) by 812 days.

(21) Appl. No.: 17/638,724

(22) PCT Filed: Aug. 24, 2020

(86) PCT No.: PCT/CN2020/110706
§ 371 (c)(1),
(2) Date: Feb. 25, 2022

(87) PCT Pub. No.: WO2021/036965
PCT Pub. Date: Mar. 4, 2021

(65) Prior Publication Data

US 2023/0065544 A1 Mar. 2, 2023

(30) Foreign Application Priority Data

Aug. 26, 2019 (CN) ........................ 201910789623.4
Jan. 7, 2020 (CN) ........................ 202010013008.7

(51) Int. Cl.

| | |
|---|---|
| ***C07D 213/26*** | (2006.01) |
| ***A01N 37/22*** | (2006.01) |
| ***A01N 43/40*** | (2006.01) |
| ***C07C 255/42*** | (2006.01) |
| ***C07D 213/16*** | (2006.01) |
| ***C07D 213/82*** | (2006.01) |
| ***C07D 213/84*** | (2006.01) |

(52) U.S. Cl.
CPC .......... *C07D 213/26* (2013.01); *A01N 37/22* (2013.01); *A01N 43/40* (2013.01); *C07C 255/42* (2013.01); *C07D 213/16* (2013.01); *C07D 213/82* (2013.01); *C07D 213/84* (2013.01)

(58) Field of Classification Search
CPC .................................................. C07D 213/26
See application file for complete search history.

(56) References Cited

U.S. PATENT DOCUMENTS

| | | | | |
|---|---|---|---|---|
| 8,686,044 B2 * | 4/2014 | Kobayashi | .......... | A61K 31/167 514/616 |
| 9,237,745 B2 * | 1/2016 | Kobayashi | .......... | A01N 43/40 |
| 9,402,395 B2 * | 8/2016 | Stoller | .......... | C07D 213/82 |
| 9,756,856 B2 * | 9/2017 | Kobayashi | .......... | C07C 255/57 |

FOREIGN PATENT DOCUMENTS

| | | |
|---|---|---|
| CN | 102112437 A | 6/2011 |
| CN | 108368030 A | 8/2018 |
| WO | 2019059412 A1 | 3/2019 |

OTHER PUBLICATIONS

Kobayashi et al (2011): STN International, CAPLUS database, Accession No. 2011: 1152241.*
International Search Report in Corresponding International Application No. PCT/CN2020/110706, mailed Oct. 29, 2020; 7 pgs.
Written Opinion in Corresponding International Application No. PCT/CN2020/110706, mailed Oct. 29, 2020; 7 pgs.

* cited by examiner

*Primary Examiner* — Golam M Shameem
(74) *Attorney, Agent, or Firm* — HAUPTMAN HAM, LLP

(57) ABSTRACT

This disclosure provides an isophthalamide compound and use thereof, wherein the compound has a structure as shown by general formula I:

Formula I

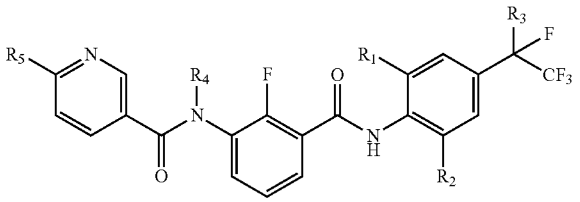

the definition of each substituent in the formula is shown in the specification. The specification also discloses use thereof as an insecticide and an animal parasite control agent.

10 Claims, No Drawings

ISOPHTHALAMIDE COMPOUND AND USE THEREOF

RELATED APPLICATIONS

The present application is a U.S. National Phase of International Application Number PCT/CN2020/110706 filed Aug. 24, 2020 and claims priority to Chinese Application Number 201910789623.4 filed Aug. 26, 2019 and Chinese Application Number 202010013008.7 filed Jan. 7, 2020.

CROSS REFERENCE TO RELATED APPLICATION

This disclosure claims priority of the Chinese patent application filed with the Chinese Patent Office with an application number of 201910789623.4 and an invention title of "BISAMIDE COMPOUND AND USE THEREOF", which is hereby incorporated herein by reference in its entirety.

This disclosure claims priority of the Chinese patent application filed with the Chinese Patent Office with an application number of 202010013008.7 and an invention title of "BISAMIDE COMPOUND AND USE THEREOF", which is hereby incorporated herein by reference in its entirety.

TECHNICAL FIELD

This disclosure relates to a compound, and in particular, to a novel isophthalamide compound and use thereof.

BACKGROUND ART

Patent CN102112437A discloses a compound CK1 (Compound No. 5-108) having an insecticidal activity.

CK1

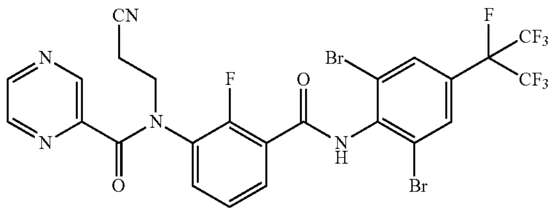

It has not been reported in the prior art about the compound represented by the general formula I herein and the insecticidal activity thereof.

SUMMARY OF THE INVENTION

An object of this disclosure is to provide an isophthalamide compound with an excellent insecticidal activity. It may be used to prepare drugs for preventing and controlling pests in agriculture and other fields, and to prepare drugs for controlling animal parasites in the field of veterinary medicine.

In order to achieve the inventive purpose of this disclosure, the following technical solutions are provided herein:

An isophthalamide compound represented by general formula I:

Formula I

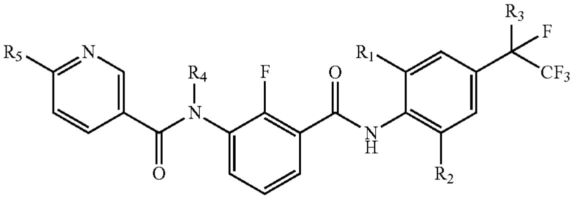

In the general formula I:

$R_1$ is selected from halogen;

$R_2$ is selected from halogen, $C_1$-$C_4$ halogenoalkyl, and $C_1$-$C_4$ halogenoalkoxy;

$R_3$ is $CF_3$ or $CF_2CF_3$;

$R_4$ is selected from cyano $C_1$-$C_4$ alkyl;

$R_5$ is selected from fluorine, difluoromethyl, and trifluoromethyl.

In a possible implementation, in the general formula I, $R_1$ is selected from halogen;

$R_2$ is selected from halogen, $C_1$-$C_2$ halogenoalkyl, and $C_1$-$C_2$ halogenoalkoxy;

$R_3$ is $CF_3$ or $CF_2CF_3$;

$R_4$ is selected from cyano $C_1$-$C_4$ alkyl;

$R_5$ is selected from fluorine, difluoromethyl, and trifluoromethyl.

In a possible implementation, in the general formula I, $R_1$ is bromine or iodine;

$R_2$ is selected from bromine, iodine, trifluoromethyl, and difluoromethoxy;

$R_3$ is $CF_3$ or $CF_2CF_3$;

$R_4$ is selected from $CH_2CN$, $CH_2CH_2CN$, $CH_2CH_2CH_2CN$, $CH_2CH_2CH_2CH_2CN$, $CH(CH_3)CN$, $CH(CH_2CH_3)CN$, $CH(CH_2CH_2CH_3)CN$, $C(CH_3)(CH_3)CN$, and $C(CH_3)(CH_2CH_3)CN$;

$R_5$ is selected from fluorine, difluoromethyl, and trifluoromethyl.

In a possible implementation, in the general formula I, $R_1$ is bromine or iodine;

$R_2$ is selected from bromine, iodine, and trifluoromethyl;

$R_3$ is $CF_3$;

$R_4$ is selected from $CH_2CN$, $CH_2CH_2CN$, $CH_2CH_2CH_2CN$, and $CH_2CH_2CH_2CH_2CN$;

$R_5$ is fluorine or trifluoromethyl.

In a possible implementation, the isophthalamide compound is selected from compounds in Table 1, and the compounds of Table 1 have the structure of general formula I and $R_1$, $R_2$, $R_3$, $R_4$ and $R_5$ are as shown in Table 1:

TABLE 1

| Compound No. | $R_1$ | $R_2$ | $R_3$ | $R_4$ | $R_5$ |
|---|---|---|---|---|---|
| 1 | Br | Br | $CF_3$ | $CH_2CN$ | F |
| 2 | Br | Br | $CF_3$ | $CH_2CH_2CN$ | F |
| 3 | Br | Br | $CF_3$ | $CH_2CH_2CH_2CN$ | F |
| 4 | Br | Br | $CF_3$ | $CH_2CH_2CH_2CH_2CN$ | F |
| 5 | Br | I | $CF_3$ | $CH_2CN$ | F |
| 6 | Br | I | $CF_3$ | $CH_2CH_2CN$ | F |
| 7 | Br | I | $CF_3$ | $CH_2CH_2CH_2CN$ | F |
| 8 | Br | I | $CF_3$ | $CH_2CH_2CH_2CH_2CN$ | F |
| 9 | Br | $CF_3$ | $CF_3$ | $CH_2CN$ | F |
| 10 | Br | $CF_3$ | $CF_3$ | $CH_2CH_2CN$ | F |
| 11 | Br | $CF_3$ | $CF_3$ | $CH_2CH_2CH_2CN$ | F |
| 12 | Br | $CF_3$ | $CF_3$ | $CH_2CH_2CH_2CH_2CN$ | F |
| 13 | I | $CF_3$ | $CF_3$ | $CH_2CN$ | F |
| 14 | I | $CF_3$ | $CF_3$ | $CH_2CH_2CN$ | F |

TABLE 1-continued

| Compound No. | $R_1$ | $R_2$ | $R_3$ | $R_4$ | $R_5$ |
|---|---|---|---|---|---|
| 15 | I | $CF_3$ | $CF_3$ | $CH_2CH_2CH_2CN$ | F |
| 16 | I | $CF_3$ | $CF_3$ | $CH_2CH_2CH_2CH_2CN$ | F |
| 17 | Br | Br | $CF_3$ | $CH_2CN$ | $CF_3$ |
| 18 | Br | Br | $CF_3$ | $CH_2CH_2CN$ | $CF_3$ |
| 19 | Br | Br | $CF_3$ | $CH_2CH_2CH_2CN$ | $CF_3$ |
| 20 | Br | Br | $CF_3$ | $CH_2CH_2CH_2CH_2CN$ | $CF_3$ |
| 21 | Br | I | $CF_3$ | $CH_2CN$ | $CF_3$ |
| 22 | Br | I | $CF_3$ | $CH_2CH_2CN$ | $CF_3$ |
| 23 | Br | I | $CF_3$ | $CH_2CH_2CH_2CN$ | $CF_3$ |
| 24 | Br | I | $CF_3$ | $CH_2CH_2CH_2CH_2CN$ | $CF_3$ |
| 25 | Br | $CF_3$ | $CF_3$ | $CH_2CN$ | $CF_3$ |
| 26 | Br | $CF_3$ | $CF_3$ | $CH_2CH_2CN$ | $CF_3$ |
| 27 | Br | $CF_3$ | $CF_3$ | $CH_2CH_2CH_2CN$ | $CF_3$ |
| 28 | Br | $CF_3$ | $CF_3$ | $CH_2CH_2CH_2CH_2CN$ | $CF_3$ |
| 29 | I | $CF_3$ | $CF_3$ | $CH_2CN$ | $CF_3$ |
| 30 | I | $CF_3$ | $CF_3$ | $CH_2CH_2CN$ | $CF_3$ |
| 31 | I | $CF_3$ | $CF_3$ | $CH_2CH_2CH_2CN$ | $CF_3$ |
| 32 | I | $CF_3$ | $CF_3$ | $CH_2CH_2CH_2CH_2CN$ | $CF_3$ |
| 33 | Br | Br | $CF_3$ | $CH_2CN$ | $CHF_2$ |
| 34 | Br | Br | $CF_3$ | $CH_2CH_2CN$ | $CHF_2$ |
| 35 | Br | Br | $CF_3$ | $CH_2CH_2CH_2CN$ | $CHF_2$ |
| 36 | Br | Br | $CF_3$ | $CH_2CH_2CH_2CH_2CN$ | $CHF_2$ |
| 37 | Br | I | $CF_3$ | $CH_2CN$ | $CHF_2$ |
| 38 | Br | I | $CF_3$ | $CH_2CH_2CN$ | $CHF_2$ |
| 39 | Br | I | $CF_3$ | $CH_2CH_2CH_2CN$ | $CHF_2$ |
| 40 | Br | I | $CF_3$ | $CH_2CH_2CH_2CH_2CN$ | $CHF_2$ |
| 41 | Br | $CF_3$ | $CF_3$ | $CH_2CN$ | $CHF_2$ |
| 42 | Br | $CF_3$ | $CF_3$ | $CH_2CH_2CN$ | $CHF_2$ |
| 43 | Br | $CF_3$ | $CF_3$ | $CH_2CH_2CH_2CN$ | $CHF_2$ |
| 44 | Br | $CF_3$ | $CF_3$ | $CH_2CH_2CH_2CH_2CN$ | $CHF_2$ |
| 45 | I | $CF_3$ | $CF_3$ | $CH_2CN$ | $CHF_2$ |
| 46 | I | $CF_3$ | $CF_3$ | $CH_2CH_2CN$ | $CHF_2$ |
| 47 | I | $CF_3$ | $CF_3$ | $CH_2CH_2CH_2CN$ | $CHF_2$ |
| 48 | I | $CF_3$ | $CF_3$ | $CH_2CH_2CH_2CH_2CN$ | $CHF_2$ |
| 49 | Br | Br | $CF_2CF_3$ | $CH_2CN$ | F |
| 50 | Br | Br | $CF_2CF_3$ | $CH_2CH_2CN$ | F |
| 51 | Br | Br | $CF_2CF_3$ | $CH_2CH_2CH_2CN$ | F |
| 52 | Br | Br | $CF_2CF_3$ | $CH_2CH_2CH_2CH_2CN$ | F |
| 53 | Br | I | $CF_2CF_3$ | $CH_2CN$ | F |
| 54 | Br | I | $CF_2CF_3$ | $CH_2CH_2CN$ | F |
| 55 | Br | I | $CF_2CF_3$ | $CH_2CH_2CH_2CN$ | F |
| 56 | Br | I | $CF_2CF_3$ | $CH_2CH_2CH_2CH_2CN$ | F |
| 57 | Br | $CF_3$ | $CF_2CF_3$ | $CH_2CN$ | F |
| 58 | Br | $CF_3$ | $CF_2CF_3$ | $CH_2CH_2CN$ | F |
| 59 | Br | $CF_3$ | $CF_2CF_3$ | $CH_2CH_2CH_2CN$ | F |
| 60 | Br | $CF_3$ | $CF_2CF_3$ | $CH_2CH_2CH_2CH_2CN$ | F |
| 61 | I | $CF_3$ | $CF_2CF_3$ | $CH_2CN$ | F |
| 62 | I | $CF_3$ | $CF_2CF_3$ | $CH_2CH_2CN$ | F |
| 63 | I | $CF_3$ | $CF_2CF_3$ | $CH_2CH_2CH_2CN$ | F |
| 64 | I | $CF_3$ | $CF_2CF_3$ | $CH_2CH_2CH_2CH_2CN$ | F |
| 65 | Br | Br | $CF_2CF_3$ | $CH_2CN$ | $CF_3$ |
| 66 | Br | Br | $CF_2CF_3$ | $CH_2CH_2CN$ | $CF_3$ |
| 67 | Br | Br | $CF_2CF_3$ | $CH_2CH_2CH_2CN$ | $CF_3$ |
| 68 | Br | Br | $CF_2CF_3$ | $CH_2CH_2CH_2CH_2CN$ | $CF_3$ |
| 69 | Br | I | $CF_2CF_3$ | $CH_2CN$ | $CF_3$ |
| 70 | Br | I | $CF_2CF_3$ | $CH_2CH_2CN$ | $CF_3$ |
| 71 | Br | I | $CF_2CF_3$ | $CH_2CH_2CH_2CN$ | $CF_3$ |
| 72 | Br | I | $CF_2CF_3$ | $CH_2CH_2CH_2CH_2CN$ | $CF_3$ |
| 73 | Br | $CF_3$ | $CF_2CF_3$ | $CH_2CN$ | $CF_3$ |
| 74 | Br | $CF_3$ | $CF_2CF_3$ | $CH_2CH_2CN$ | $CF_3$ |
| 75 | Br | $CF_3$ | $CF_2CF_3$ | $CH_2CH_2CH_2CN$ | $CF_3$ |
| 76 | Br | $CF_3$ | $CF_2CF_3$ | $CH_2CH_2CH_2CH_2CN$ | $CF_3$ |
| 77 | I | $CF_3$ | $CF_2CF_3$ | $CH_2CN$ | $CF_3$ |
| 78 | I | $CF_3$ | $CF_2CF_3$ | $CH_2CH_2CN$ | $CF_3$ |
| 79 | I | $CF_3$ | $CF_2CF_3$ | $CH_2CH_2CH_2CN$ | $CF_3$ |
| 80 | I | $CF_3$ | $CF_2CF_3$ | $CH_2CH_2CH_2CH_2CN$ | $CF_3$ |
| 81 | Br | Br | $CF_2CF_3$ | $CH_2CN$ | $CHF_2$ |
| 82 | Br | Br | $CF_2CF_3$ | $CH_2CH_2CN$ | $CHF_2$ |
| 83 | Br | Br | $CF_2CF_3$ | $CH_2CH_2CH_2CN$ | $CHF_2$ |
| 84 | Br | Br | $CF_2CF_3$ | $CH_2CH_2CH_2CH_2CN$ | $CHF_2$ |
| 85 | Br | I | $CF_2CF_3$ | $CH_2CN$ | $CHF_2$ |
| 86 | Br | I | $CF_2CF_3$ | $CH_2CH_2CN$ | $CHF_2$ |
| 87 | Br | I | $CF_2CF_3$ | $CH_2CH_2CH_2CN$ | $CHF_2$ |
| 88 | Br | I | $CF_2CF_3$ | $CH_2CH_2CH_2CH_2CN$ | $CHF_2$ |
| 89 | Br | $CF_3$ | $CF_2CF_3$ | $CH_2CN$ | $CHF_2$ |
| 90 | Br | $CF_3$ | $CF_2CF_3$ | $CH_2CH_2CN$ | $CHF_2$ |
| 91 | Br | $CF_3$ | $CF_2CF_3$ | $CH_2CH_2CH_2CN$ | $CHF_2$ |

TABLE 1-continued

| Compound No. | $R_1$ | $R_2$ | $R_3$ | $R_4$ | $R_5$ |
|---|---|---|---|---|---|
| 92 | Br | $CF_3$ | $CF_2CF_3$ | $CH_2CH_2CH_2CH_2CN$ | $CHF_2$ |
| 93 | I | $CF_3$ | $CF_2CF_3$ | $CH_2CN$ | $CHF_2$ |
| 94 | I | $CF_3$ | $CF_2CF_3$ | $CH_2CH_2CN$ | $CHF_2$ |
| 95 | I | $CF_3$ | $CF_2CF_3$ | $CH_2CH_2CH_2CN$ | $CHF_2$ |
| 96 | I | $CF_3$ | $CF_2CF_3$ | $CH_2CH_2CH_2CH_2CN$ | $CHF_2$. |

In a possible implementation, the isophthalamide compound is selected from compounds in Table 2, and the compounds of Table 2 have the structure of general formula I and $R_1$, $R_2$, $R_3$, $R_4$ and $R_5$ are as shown in Table 2:

TABLE 2

| Compound No. | $R_1$ | $R_2$ | $R_3$ | $R_4$ | $R_5$ |
|---|---|---|---|---|---|
| 1 | Br | Br | $CF_3$ | $CH_2CN$ | F |
| 2 | Br | Br | $CF_3$ | $CH_2CH_2CN$ | F |
| 3 | Br | Br | $CF_3$ | $CH_2CH_2CH_2CN$ | F |
| 4 | Br | Br | $CF_3$ | $CH_2CH_2CH_2CH_2CN$ | F |
| 5 | Br | I | $CF_3$ | $CH_2CN$ | F |
| 6 | Br | I | $CF_3$ | $CH_2CH_2CN$ | F |
| 7 | Br | I | $CF_3$ | $CH_2CH_2CH_2CN$ | F |
| 8 | Br | I | $CF_3$ | $CH_2CH_2CH_2CH_2CN$ | F |
| 9 | Br | $CF_3$ | $CF_3$ | $CH_2CN$ | F |
| 10 | Br | $CF_3$ | $CF_3$ | $CH_2CH_2CN$ | F |
| 11 | Br | $CF_3$ | $CF_3$ | $CH_2CH_2CH_2CN$ | F |
| 12 | Br | $CF_3$ | $CF_3$ | $CH_2CH_2CH_2CH_2CN$ | F |
| 13 | I | $CF_3$ | $CF_3$ | $CH_2CN$ | F |
| 14 | I | $CF_3$ | $CF_3$ | $CH_2CH_2CN$ | F |
| 15 | I | $CF_3$ | $CF_3$ | $CH_2CH_2CH_2CN$ | F |
| 16 | I | $CF_3$ | $CF_3$ | $CH_2CH_2CH_2CH_2CN$ | F |
| 17 | Br | Br | $CF_3$ | $CH_2CN$ | $CF_3$ |
| 18 | Br | Br | $CF_3$ | $CH_2CH_2CN$ | $CF_3$ |
| 19 | Br | Br | $CF_3$ | $CH_2CH_2CH_2CN$ | $CF_3$ |
| 20 | Br | Br | $CF_3$ | $CH_2CH_2CH_2CH_2CN$ | $CF_3$ |
| 21 | Br | I | $CF_3$ | $CH_2CN$ | $CF_3$ |
| 22 | Br | I | $CF_3$ | $CH_2CH_2CN$ | $CF_3$ |
| 23 | Br | I | $CF_3$ | $CH_2CH_2CH_2CN$ | $CF_3$ |
| 24 | Br | I | $CF_3$ | $CH_2CH_2CH_2CH_2CN$ | $CF_3$ |
| 25 | Br | $CF_3$ | $CF_3$ | $CH_2CN$ | $CF_3$ |
| 26 | Br | $CF_3$ | $CF_3$ | $CH_2CH_2CN$ | $CF_3$ |
| 27 | Br | $CF_3$ | $CF_3$ | $CH_2CH_2CH_2CN$ | $CF_3$ |
| 28 | Br | $CF_3$ | $CF_3$ | $CH_2CH_2CH_2CH_2CN$ | $CF_3$ |
| 29 | I | $CF_3$ | $CF_3$ | $CH_2CN$ | $CF_3$ |
| 30 | I | $CF_3$ | $CF_3$ | $CH_2CH_2CN$ | $CF_3$ |
| 31 | I | $CF_3$ | $CF_3$ | $CH_2CH_2CH_2CN$ | $CF_3$ |
| 32 | I | $CF_3$ | $CF_3$ | $CH_2CH_2CH_2CH_2CN$ | $CF_3$. |

An intermediate compound for preparing the above isophthalamide compound, wherein the intermediate compound is represented by general formula II:

Formula II

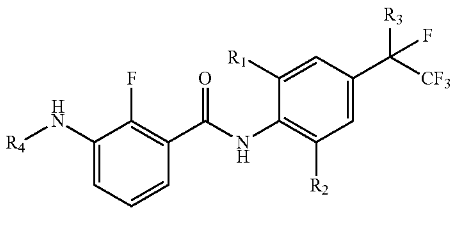

In the general formula II:

$R_1$ is selected from halogen;

$R_2$ is selected from halogen, $C_1$-$C_4$ halogenoalkyl, and $C_1$-$C_4$ halogenoalkoxy;

$R_3$ is $CF_3$ or $CF_2CF_3$;

$R_4$ is selected from cyano $C_1$-$C_4$ alkyl.

In a possible implementation, in the general formula III, $R_1$ is selected from halogen;

$R_2$ is selected from halogen, $C_1$-$C_2$ halogenoalkyl, and $C_1$-$C_2$ halogenoalkoxy;

$R_3$ is $CF_3$ or $CF_2CF_3$;

$R_4$ is selected from cyano $C_1$-$C_4$ alkyl.

In a possible implementation, in the general formula II, $R_1$ is bromine or iodine;

$R_2$ is selected from bromine, iodine, trifluoromethyl, and difluoromethoxy;

$R_3$ is $CF_3$ or $CF_2CF_3$;

$R_4$ is selected from $CH_2CN$, $CH_2CH_2CN$, $CH_2CH_2CH_2CN$, $CH_2CH_2CH_2CH_2CN$, $CH(CH_3)CN$, $CH(CH_2CH_3)CN$, $CH(CH_2CH_2CH_3)CN$, $C(CH_3)(CH_3)CN$, and $C(CH_3)(CH_2CH_3)CN$;

In a possible implementation, in the general formula II, $R_1$ is bromine or iodine;

$R_2$ is selected from bromine, iodine, and trifluoromethyl;

$R_3$ is $CF_3$;

$R_4$ is selected from $CH_2CN$, $CH_2CH_2CN$, $CH_2CH_2CH_2CN$, and $CH_2CH_2CH_2CH_2CN$.

In a possible implementation, the intermediate compound is selected from the compounds in Table 3, and the compounds of Table 3 have the structure of general formula II and $R_1$, $R_2$, $R_3$ and $R_4$ are as shown in Table 3:

TABLE 3

| No. | $R_1$ | $R_2$ | $R_3$ | $R_4$ |
|---|---|---|---|---|
| II.1 | Br | Br | $CF_3$ | $CHCN$ |
| II.2 | Br | Br | $CF_3$ | $CH_2CH_2CN$ |
| II.3 | Br | Br | $CF_3$ | $CH_2CH_2CH_2CN$ |
| II.4 | Br | Br | $CF_3$ | $CH_2CH_2CH_2CH_2CN$ |
| II.5 | Br | I | $CF_3$ | $CH_2CN$ |
| II.6 | Br | I | $CF_3$ | $CH_2CH_2CN$ |
| II.7 | Br | I | $CF_3$ | $CH_2CH_2CH_2CN$ |
| II.8 | Br | I | $CF_3$ | $CH_2CH_2CH_2CH_2CN$ |
| II.9 | Br | $CF_3$ | $CF_3$ | $CH_2CN$ |
| II.10 | Br | $CF_3$ | $CF_3$ | $CH_2CH_2CN$ |
| II.11 | Br | $CF_3$ | $CF_3$ | $CH_2CH_2CH_2CN$ |
| II.12 | Br | $CF_3$ | $CF_3$ | $CH_2CH_2CH_2CH_2CN$ |
| II.13 | I | $CF_3$ | $CF_3$ | $CH_2CN$ |
| II.14 | I | $CF_3$ | $CF_3$ | $CH_2CH_2CN$ |
| II.15 | I | $CF_3$ | $CF_3$ | $CH_2CH_2CH_2CN$ |
| II.16 | I | $CF_3$ | $CF_3$ | $CH_2CH_2CH_2CH_2CN$ |
| II.17 | Br | Br | $CF_2CF_3$ | $CH_2CN$ |
| II.18 | Br | Br | $CF_2CF_3$ | $CH_2CH_2CN$ |
| II.19 | Br | Br | $CF_2CF_3$ | $CH_2CH_2CH_2CN$ |
| II.20 | Br | Br | $CF_2CF_3$ | $CH_2CH_2CH_2CH_2CN$ |
| II.21 | Br | I | $CF_2CF_3$ | $CH_2CN$ |
| II.22 | Br | I | $CF_2CF_3$ | $CH_2CH_2CN$ |
| II.23 | Br | I | $CF_2CF_3$ | $CH_2CH_2CH_2CN$ |
| II.24 | Br | I | $CF_2CF_3$ | $CH_2CH_2CH_2CH_2CN$ |
| II.25 | Br | $CF_3$ | $CF_2CF_3$ | $CH_2CN$ |
| II.26 | Br | $CF_3$ | $CF_2CF_3$ | $CH_2CH_2CN$ |
| II.27 | Br | $CF_3$ | $CF_2CF_3$ | $CH_2CH_2CH_2CN$ |
| II.28 | Br | $CF_3$ | $CF_2CF_3$ | $CH_2CH_2CH_2CH_2CN$ |
| II.29 | I | $CF_3$ | $CF_2CF_3$ | $CH_2CN$ |
| II.30 | I | $CF_3$ | $CF_2CF_3$ | $CH_2CH_2CN$ |
| II.31 | I | $CF_3$ | $CF_2CF_3$ | $CH_2CH_2CH_2CN$ |
| II.32 | I | $CF_3$ | $CF_2CF_3$ | $CH_2CH_2CH_2CH_2CN$. |

An intermediate compound for preparing the above isophthalamide compound, wherein the compound is represented by general formula III:

Formula III

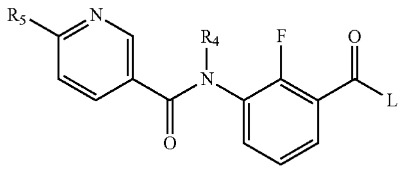

In the general formula III:

$R_4$ is selected from cyano $C_1$-$C_4$ alkyl;

$R_5$ is selected from fluorine, difluoromethyl, and trifluoromethyl;

L is selected from halogen and hydroxyl.

In a possible implementation, in the general formula III, $R_4$ is selected from $CH_2CN$, $CH_2CH_2CN$, $CH_2CH_2CH_2CN$, $CH_2CH_2CH_2CH_2CN$, $CH(CH_3)CN$, $CH(CH_2CH_3)CN$, $CH(CH_2CH_2CH_3)CN$, $C(CH_3)(CH_3)CN$, and $C(CH_3)(CH_2CH_3)CN$;

$R_5$ is selected from fluorine, difluoromethyl, and trifluoromethyl;

L is selected from halogen and hydroxyl.

In a possible implementation, the intermediate compound is selected from the compounds in Table 4, and the compounds of Table 4 have the structure of general formula III and $R_4$, $R_5$, and L are as shown in Table 4:

TABLE 4

| No. | $R_4$ | $R_5$ | L |
|---|---|---|---|
| III.1 | $CH_2CN$ | F | Cl |
| III.2 | $CH_2CH_2CN$ | F | Cl |
| III.3 | $CH_2CH_2CH_2CN$ | F | Cl |
| III.4 | $CH_2CH_2CH_2CH_2CN$ | F | Cl |
| III.5 | $CH_2CN$ | F | OH |
| III.6 | $CH_2CH_2CN$ | F | OH |
| III.7 | $CH_2CH_2CH_2CN$ | F | OH |
| III.8 | $CH_2CH_2CH_2CH_2CN$ | F | OH |
| III.9 | $CH_2CN$ | $CF_3$ | Cl |
| III.10 | $CH_2CH_2CN$ | $CF_3$ | Cl |
| III.11 | $CH_2CH_2CH_2CN$ | $CF_3$ | Cl |
| III.12 | $CH_2CH_2CH_2CH_2CN$ | $CF_3$ | Cl |
| III.13 | $CH_2CN$ | $CF_3$ | OH |
| III.14 | $CH_2CH_2CN$ | $CF_3$ | OH |
| III.15 | $CH_2CH_2CH_2CN$ | $CF_3$ | OH |
| III.16 | $CH_2CH_2CH_2CH_2CN$ | $CF_3$ | OH. |

The compound of general formula I of this disclosure may be prepared according to the following two methods (the groups in the formulas are defined as before unless otherwise specified, wherein LG=Cl, Br or I):

Method I:

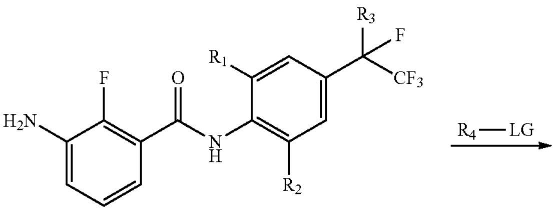

IV

-continued

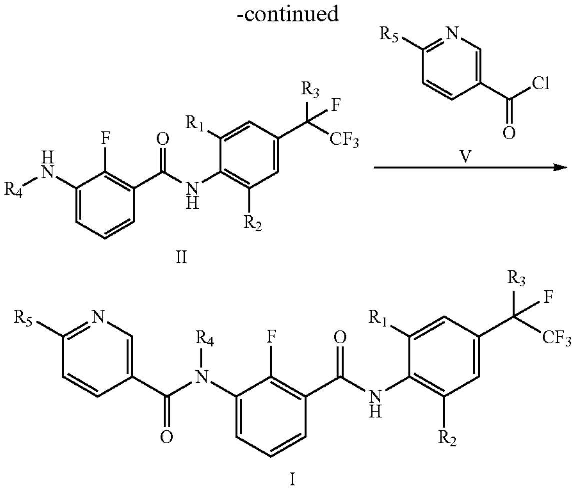

II

I

The compound of the general formula II may be obtained by reaction of the compound of the general formula IV with the halogenated compound $R_4$-LG in a suitable solvent at a temperature from −10° C. to the boiling point of the solvent for 0.5-48 hours, in the presence of a base and a catalyst. The compound of general formula I may be obtained by reaction of the compound of formula II with the compound of general formula V in a suitable solvent at a temperature from −10° C. to the boiling point of the solvent for 0.5-48 hours, in the presence of a base and a catalyst. Suitable solvents in the above steps may be same or different, and may be: aromatic hydrocarbons such as benzene, toluene and xylene; ketones such as acetone, methyl ethyl ketone and methyl isobutyl ketone; halogenated hydrocarbons such as chloroform and dichloromethane; esters such as methyl acetate and ethyl acetate; ethers such as tetrahydrofuran, dioxane, diethyl ether, 1,2-dimethoxyethane; polar solvents such as water, acetonitrile, N,N-dimethylformamide, N-methylpyrrolidone and dimethyl sulfoxide, or mixed solvents of the above solvents. In the above steps, the bases may be same or different, and may be organic bases such as triethylamine, pyridine, DBU, 4-dimethylaminopyridine; alkali metal hydrides such as sodium hydride, potassium hydride; alkali metal hydroxides such as sodium hydroxide and potassium hydroxide; alkaline earth metal hydroxides such as calcium hydroxide; alkali metal carbonates such as sodium carbonate and potassium carbonate, alkali metal bicarbonates such as sodium bicarbonate; metal alkoxides such as sodium methoxide, sodium ethoxide, potassium ethoxide, potassium tert-butoxide, sodium tert-butoxide. The catalysts in each of the above steps may be same or different, and may be: potassium iodide, sodium iodide, potassium fluoride, sodium fluoride, potassium bromide or sodium bromide, or the like.

The compound of general formula IV may be prepared according to known methods, for example, methods reported in WO20110201687, WO2011093415, WO2005021488, WO2005073165, WO2006137395, JP2007099761, WO2008000438, WO2008074427, WO2008107091, WO2010013567, WO2010018714, WO2010090282, WO2010127926, WO2010127928, JP2011063549, WO2012020483, WO2012020484, WO2012077221, WO2012164698, WO2013050261, WO2014069665, WO2014067838, WO2014161848, WO2014161850, WO2015097091 or WO2015097094, or other literatures. The halogenated compound $R_4$-LG the compound of general formula V and the base are usually commercially available, and may also be prepared according to conventional methods.

Method II:

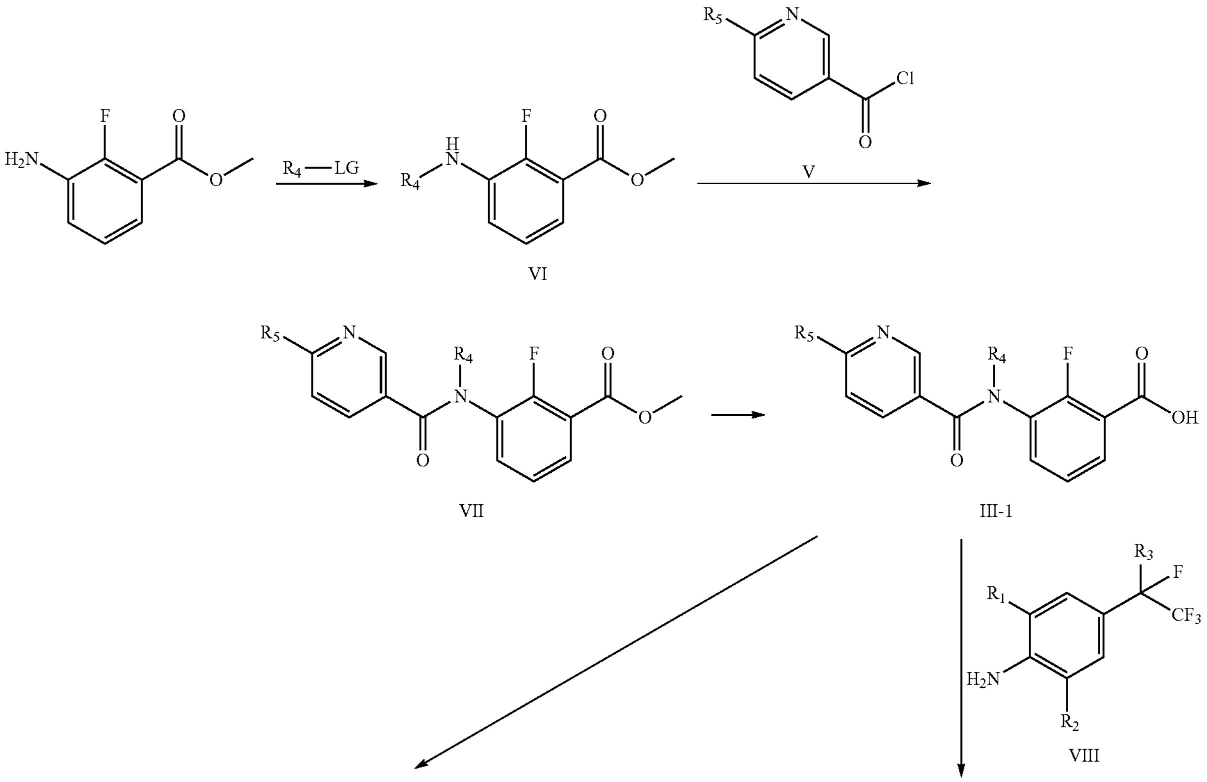

VI

VII

III-1

VIII

-continued

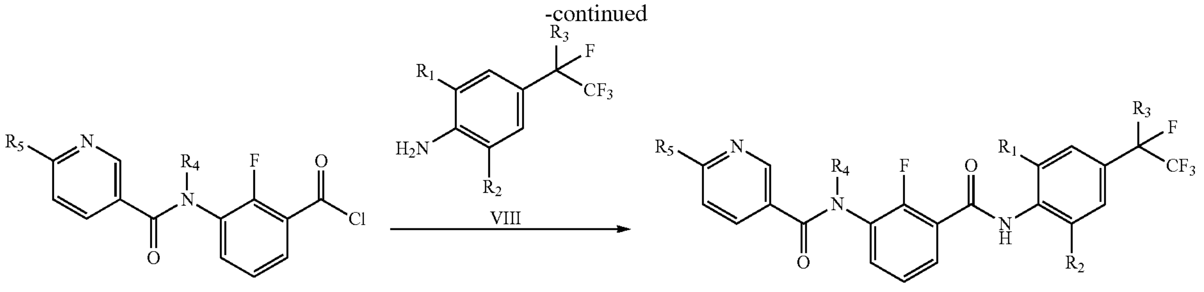

III-2

I (1) Preparation of the Compound of General Formula VI and the Compound of General Formula VII The compound of the general formula VI may be obtained by reaction of methyl 3-amino-2-fluorobenzoate with the halogenated compound $R_4$-LG in a suitable solvent at a temperature from −10° C. to the boiling point of the solvent for 0.5-48 hours, in the presence of a base. The compound of general formula VII may be obtained by reaction of the compound of formula VI with the compound of general formula V in a suitable solvent at a temperature from −10° C. to the boiling point of the solvent for 0.5-48 hours, in the presence of a base. Suitable solvents in the above reaction may be: aromatic hydrocarbons such as benzene, toluene and xylene; ketones such as acetone, methyl ethyl ketone and methyl isobutyl ketone; halogenated hydrocarbons such as chloroform and dichloromethane; esters such as methyl acetate and ethyl acetate; ethers such as tetrahydrofuran, dioxane, diethyl ether, 1,2-dimethoxyethane; polar solvents such as water, acetonitrile, N,N-dimethylformamide, N-methylpyrrolidone and dimethyl sulfoxide, or mixed solvents of the above solvents. The bases may be organic bases such as triethylamine, pyridine, DBU, 4-dimethylaminopyridine; alkali metal hydrides such as sodium hydride, potassium hydride; alkali metal hydroxides such as sodium hydroxide and potassium hydroxide; alkaline earth metal hydroxides such as calcium hydroxide; alkali metal carbonates such as sodium carbonate and potassium carbonate, alkali metal bicarbonates such as sodium bicarbonate; metal alkoxides such as sodium methoxide, sodium ethoxide, potassium ethoxide, potassium tert-butoxide, and sodium tert-butoxide.

(2) Preparation of the Compound of General Formula III-1 and the Compound of General Formula III-2

The compound of general formula VII may be hydrolyzed to prepare the compound of general formula III-1 in the presence of an alkaline substance at a temperature from −10° C. to the boiling point of the solvent for 0.5-48 hours. A suitable base may be lithium hydroxide, sodium hydroxide or potassium hydroxide, and a suitable solvent may be any one of water, methanol, ethanol, tetrahydrofuran and dioxane, or a mixed solvent of at least two of them.

The compound of general formula III-2 may be prepared by reaction of the compound of general formula III-1 with thionyl chloride, oxalyl chloride, phosgene, phosphoryl chloride, phosphorous pentachloride, phosphorous trichloride, triphosgene, or the like by a known method.

(3) Preparation of the Compound of General Formula I

The compound of the general formula I may be obtained by reaction of the compound of the general formula III-1 or III-2 with the compound of the general formula VIII in a suitable solvent at a temperature from −70° C. to the boiling point of the solvent for 0.5-48 hours, in the presence of a base. Suitable solvents may be: aromatic hydrocarbons such as benzene, toluene and xylene; ketones such as acetone, methyl ethyl ketone and methyl isobutyl ketone; halogenated hydrocarbons such as chloroform and dichloromethane; esters such as methyl acetate and ethyl acetate; ethers such as tetrahydrofuran, dioxane, diethyl ether, 1,2-dimethoxyethane; polar solvents such as water, acetonitrile, N,N-dimethylformamide, N-methylpyrrolidone and dimethyl sulfoxide, or mixed solvents of the above solvents. The bases may be organic bases such as trimethylamine, triethylamine, diisopropylethylamine, tri-n-butylamine, pyridine, DBU, 4-dimethylaminopyridine; alkali metal hydrides such as sodium hydride, potassium hydride; alkali metal hydroxides such as sodium hydroxide and potassium hydroxide; alkaline earth metal hydroxides such as calcium hydroxide; alkali metal carbonates such as sodium carbonate and potassium carbonate, alkali metal bicarbonates such as sodium bicarbonate; metal alkoxides such as sodium methoxide, sodium ethoxide, potassium ethoxide, potassium tert-butoxide, and sodium tert-butoxide.

The embodiments of this disclosure also provide use of the above isophthalamide compounds in the preparation of an insecticide.

In a possible implementation, the insecticide is used to control one or more of the following insects:

Beetles (Coleopteran), such as *Callosobruchus Chinensis, Sitophilus zeamais, Tribolium Castaneum, Epilachna vigintioctomaculata, Agriotes ogurae fuscicollis, Anomala rufocuprea, Leptinotarsa decemlineata, Diabrotica* spp., *Monochamus alternatus endai, Lissorhoptrus oryzophilus, Lyctus bruneus;*

Lepidopteran pests, such as *Lymantria dispar, Malacosoma neustria, Pieris rapae crucivora, Spodoptera litura, Mamestra brassicae, Chilo suppressalis, Ostrinia nubilalis, Cadra cautella*, chyanokokakumonhamaki (*Adoxophyes honmai*), *Cydia pomonella, Agrotis segetum, Galleria mellonella, Plutella xylostella, Heliothis virescens, Phyllocnistis citrella;*

Hemipterous pests, such as *Nephotettix cincticeps, Nilaparvata lugens, Pseudococcus comstocki, Unaspis yanonensis, Myzus persicas, Aphis pomi, Aphis gossypii, Lipaphis erysimi, Stephanitis nashi, Nezara* spp., *Trialeurodes vaporariorum, Pshylla* spp.;

Thysanoptera pests, such as *Thrips palmi* and *Franklinella occidentalis;*

Orthopteran pests, such as *Gryllotalpa Africana* and *Locusta migratoria;*

Blattarian pests, such as *Blattella germanica, Periplaneta americana, Reticulitermes speratus, Coptotermes formosanus;*

Dipterous pests, such as *Musca domestica, Aedesaegypti, Delia platura, Culex pipiens pallens, Anopheles sinensis, Culex tritaeniorhynchus, Liriomyza trifolii*, or the like;

Agricultural pest mites, such as *Tetranychus cinnabarinus, Tetrahychus urticae, Panonychus citri, Aculops pelekassi, Tarsonemus* spp., or the like.

In a possible implementation, the insecticide is used to control one or more of *Leucania separata, Plutella xylostella*, and *Chilo suppressalis.*

The embodiments of this disclosure also provide an insecticide formulation, comprising the above isophthalamide compound as an active component, and also one or more adjuvants.

In a possible implementation, the insecticide formulation is selected from the following dosage forms: solution, emulsion, wettable powder, granular wettable powder, suspension, powder, foam, ointment, tablet, granule, aerosol, natural agent impregnated with an active compound, a synthetic agent impregnated with an active compound, a microcapsule, a seed coating agent, a formulation equipped with a combustion device (the combustion device may be a chimney, a mist tube, a pot and coils, etc.) and ULV (cold mist, hot mist), or the like. These insecticide formulation or animal parasite control agent may be prepared by known methods, for example, by mixing an active ingredient with a filler (such as a liquid diluent or carrier, a liquefied gas diluent or carrier, a solid diluent or carrier), and optionally mixing with a surfactant (an emulsifier and/or a dispersant and/or a foaming agent) or the like. In a possible implementation, the adjuvant includes one or more of the followings: a filler (such as: a liquid diluent or carrier, a liquefied gas diluent or carrier, a solid diluent or carrier), a surfactant (for example, an emulsifier and/or a dispersant and/or a foaming agent), an adhesive, or a colorant;

The liquid diluent or carrier may include, for example, an aromatic hydrocarbon (xylene, toluene, alkyl naphthalene, etc.), a chlorinated aromatic hydrocarbon or chlorinated aliphatic hydrocarbon (such as chlorobenzene, vinyl chloride, methylene chloride, etc.), an aliphatic hydrocarbon (such as cyclohexane or paraffin wax (such as a mineral oil fraction)), an alcohol (such as butanol, ethylene glycol, and an ether or a ester thereof, etc.), a ketone (such as acetone, methyl ethyl ketone, methyl isobutyl ketone, cyclohexanone, etc.), a strong polar solvent (such as dimethyl formamide, dimethyl sulfoxide), water, or the like. When water is used as the filler, for example, an organic solvent may be used as a cosolvent;

The liquefied gas diluent or carrier may include a liquefied gas diluent or carrier that exists in gaseous form at atmospheric pressure and temperature, for example, propane, nitrogen, carbon dioxide, and an aerosol propellant such as a halogenated hydrocarbon;

The solid diluent may include a pulverized natural mineral (such as kaolin, clay, talc, chalk, quartz, attapulgite, montmorillonite, or diatomaceous earth) and a pulverized synthetic mineral (such as finely dispersed silicic acid, alumina and silicate), or the like;

The emulsifier and/or foaming agent may include a nonionic emulsifier and an anionic emulsifier (such as a polyoxyethylene fatty acid ester, a polyoxyethylene fatty acid alcohol ethers (such as alkyl aryl polyglycol ether), an alkyl sulfonate, an alkyl sulfate and an aryl sulfonate) and an albumin hydrolysate, or the like;

The dispersant may include lignin sulfite waste liquid and methyl cellulose;

The binder may include carboxymethyl cellulose, a natural or synthetic polymer (such as gum arabic, polyvinyl alcohol, polyvinyl acetate);

The colorant may include an inorganic pigment (such as iron oxide, titanium oxide, and prussian blue), an organic dye such as an alizarin dye, an azo dye, or a metal phthalocyanine dye; and a trace element such as an iron salt, a manganese salt, a boron salt, a copper salt, a cobalt salt, a molybdenum salt or a zinc salt.

In addition, the isophthalamide compound of this disclosure may be present as a mixture with a synergist, wherein the synergist itself is not necessarily be active. More specifically, it is a compound that enhances the activity of the active compound.

In a possible implementation, the amount of the isophthalamide compound contained in the insecticide formulation is 0.1 to 99% by weight, optionally 0.5 to 90% by weight.

The embodiments of this disclosure also provide an insecticide composition, including a mixture of the foregoing isophthalamide compound and another active compound (such as an insecticide, a poison bait, a disinfectant, an acaricide, a nematicide, a fungicide, a growth regulator, a herbicide).

The mixture may be provided in the form of a crude drug, or may be provided in the form of a commercially available useful formulation or a usage form prepared from a formulation thereof.

The embodiments of this disclosure also provide a method for controlling an agricultural or forestry pest, including the following steps: applying an effective dose of a material to the pest to be controlled or a growth medium thereof, where the material is one or more selected from the following group: the foregoing isophthalamide compound, the foregoing insecticide formulation, and the foregoing insecticide composition.

The embodiments of this disclosure also provide use of the foregoing isophthalamide compound for preparing an animal parasite control agent. In the field of veterinary medicine, that is, in veterinary science, the isophthalamide compound of this disclosure may be effectively used to combat a variety of harmful animal parasites, especially endoparasites and ectoparasites.

In a possible implementation, the animal parasites include one or more of the followings:

Anoplurida, such as *Haematopinus* spp., *Linognathus* spp., *Pediculus* spp., *Phtirus* spp, and *Solenopotes* spp.; where in particular, representative examples include *Linognathus setosus, Solenopotes capillatus;*

Mallopha (*Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis gida*), and Amblycerina and Ischnocerin, for example, *Trimenopon* spp., *Menopon* spp., *Trinoton* spp., *Bovicola* spp., *Werneckiella* spp., *Lepikentron* spp., *Damalina* spp., *Trichodectes* spp., and *Felicola* spp.; where in particular, representative examples include *Bovicola bovis, Bovicola ovis, Bovicola limbata, Damalina bovis, Trichodectes canis, Felicola subrostratus, Bovicola caprae, Lepikentron ovis, Werneckiella equi;*

Diptera and its Nematocerina and Brachycerina, for example, *Aedes* spp., *Anopheles* spp., *Culex* spp., *Simulium* spp, *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; where in particular, representative examples include *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis*, Haematopotaitalica, *Musca autumnalis, Musca domestica, Haematobia irritans* irritans, *Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus interrnis, Gasterophilus nasalis, Gasterophilus nigricornis, Gasterophilus pecorum, Braula coeca;*

Siphonapterida, for example, *Pulex* spp., *Ctenocephalides* spp., *Tunga* spp., *Xenopsylla* spp., *Ceratophyllus* spp.; where in particular, representative examples include *Ctenocephalides canis, Ctenocephalides felis, Pulex irritans, Tunga penetrans, Xenopsylla cheopis;*

Heteropterida, for example, *Cimex* spp., *Triatoma* spp., *Rhodnius* spp., *Panstrongylus* spp.;

Blattarida, for example, *Blatta orientalis, Periplaneta americana, Blatta germanica, Supella* spp. (for example, *Suppella longipalpa*);

Acari (or Acarina), Metastigmata and Mesostigmata, for example, *Argas* spp., *Ornithodorus* spp., *Otobius* spp., *Ixodes* spp., *Amblyomma* spp., *Rhipicephalus* (Boophilus) spp., *Dermacentor* spp., *Haemophysalis* spp., *Hyalomma* spp., *Dermanyssus* spp., *Rhipicephalus* spp. (the original genus of heterotopic parasitic mites), *Ornithonyssus* spp.,

*Pneumonyssus* spp., *Pneumonyssus* spp., *Railietia* spp., *Pneumonyssus* spp., *Sternostoma* spp., *Varroa* spp., *Acarapis* spp.; where in particular, representative examples include *Argas persicus, Argas reflexus, Ornithodorus moubata, Otobius megnini, Rhipicephalus* (Boophilus) *microplus, Rhipicephalus* (Boophilus) *decoloratus, Rhipicephalus* (Boophilus) *annulatus, Rhipicephalus* (Boophilus) *calceratus, Hyalomma anatolicum*, Hyalommaaegypticum, *Hyaloma marginatum, Hyalomma transiens*, Rhipicephalusevertsi, *Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsconi;*

Actinedida (Prostigmata and Acaridida (Astigmata)), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; in particular, *C. heyletiella yasguri, C. heyletiella blakei, Demodex canis, Demodex bovis, Demodex ovis, Demodex caprae, Demodex equi, Demodex caballi, Demodex suis, Neotrombicula autumnalis*, Neotrombiculadesaleli, *Neoschonegastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi;*

Nematodes, such as *Meloidogyne incognita, Bursaphelenchus xylophilus, Aphelenchoides besseyi, Heterodera glycines, Pratylenchus* spp., etc.;

Arthropods, worms and malaria parasites that invade animals. Controlling arthropods, worms and/or malaria parasites may reduce the mortality of domestic animals and improve the productivity (meat, milk, hair, skin, eggs, and honey) and health of animals.

In a possible implementation, the animal parasite control agent is used to control one or more of cat fleas and American dog ticks.

In a possible implementation, the animal includes one or more of the followings: an agricultural animal, such as cow, sheep, goat, horse, pig, donkey, camel, buffalo, rabbit, chicken, turkey, duck, geese, farmed fish, bee, or the like; also includes pets called companion animals, such as dog, cat, caged bird, and ornamental fish; also includes an animal used in experiments, such as hamster, guinea pig, rat, and mice.

The embodiments of this disclosure also provide an animal parasite control agent, containing the above isophthalamide compound as an active component, and also one or more adjuvants.

In a possible implementation, the animal parasite control agent is selected from the following dosage forms: tablet, capsule, draught, drinkable drug, granule, ointment and pill, suppository, injection (muscle, subcutaneous, intravenous, intraperitoneal, etc), liniment, aerosol, non-pressure spray (such as pump spray and an atomized spray).

In a possible implementation, the amount of the foregoing active component contained in the animal parasite control agent is 1% to 80% by weight.

The embodiments of this disclosure also provide an animal parasite control composition, including a mixture of the foregoing isophthalamide compound and another animal parasite control active compound (such as an acaricide, an insecticide, a parasiticide, or antimalarial agent). The mixture may be provided in the form of a crude drug, or may be provided in the form of a commercially available useful formulation or a usage form prepared from a formulation thereof.

The embodiments of this disclosure also provide a method for controlling animal parasites, including the following steps: applying an effective dose of a material to an animal parasite or a growth medium thereof that needs to be controlled, wherein the material is one or more selected from the following group: the foregoing isophthalamide compound; the foregoing animal parasite control agent; or the foregoing animal parasite control composition. For example, it is administered by means of enteral administration through tablet, capsule, draught, drinkable drug, granule, ointment, pill, suppository; skin-based non-intestinal administration, such as injection (such as muscle, subcutaneous, intravenous, or intraperitoneal), implantation, nasal administration, including bathing or soaking, spraying, pouring, dripping, washing and dusting, and through the use of a model product containing an active compound, such as a collar, an ear tag, a tag, a leg brace, a net, a marker, or the like. The active compound of this disclosure has low toxicity and may be safely used for a warm-blooded animal.

Beneficial Effects

The isophthalamide compound of this disclosure has an unexpectedly excellent insecticidal effect, and also exhibits a suitable control effect against toxic pests, and is not phytotoxic to cultivated crop plants. In addition, the compound of this disclosure may be used to control various pests, such as harmful sucking insects, chewing insects, and other plant parasitic pests, stored grain pests, sanitary pests, or the like, and may be used to disinfect and kill them.

DETAILED DESCRIPTION OF THE INVENTION

In order to make the objects, technical solutions, and advantages of the embodiments of this disclosure clearer, the technical solutions in the embodiments of this disclosure will be described clearly and completely below. It is apparent that the described embodiments are part of the embodiments of this disclosure, but not exhaustive. Based on the embodiments of this disclosure, all other embodiments obtained by those of ordinary skill in the art without creative work shall fall within the protection scope of this disclosure.

In addition, in order to better illustrate this disclosure, numerous specific details are given in the following specific embodiments. Those skilled in the art should understand that this disclosure may also be implemented without certain specific details. In some embodiments, the raw materials, elements, methods, means, or the like that are well known to those skilled in the art are not described in detail in order to highlight the gist of this disclosure.

Unless otherwise expressly stated, throughout the specification and claims, the term "comprise (comprising)" or a variation thereof such as "include (including)" or "contain (containing)" is construed as including the stated element or component, without excluding other elements or other components.

Unless otherwise noted, all starting materials used are commercially available.

In this disclosure, the terms used have the following meanings:

Halogen: fluorine, chlorine, bromine or iodine.

Halogenoalkyl: straight or branched chain alkyl, and the hydrogen atoms on these alkyl groups may be partially or completely replaced by halogens, such as difluoromethyl ($CHF_2$), trifluoromethyl ($CF_3$), or the like.

Halogenoalkoxy: The hydrogen atoms on the alkoxy group may be partially or completely replaced by halogen, such as difluoromethoxy ($OCHF_2$), trifluoromethoxy ($OCF_3$) or the like.

Cyanoalkyl: straight or branched chain alkyl, and the hydrogen atoms on these alkyl groups may be partially or completely replaced by cyano groups. $C_1$-$C_4$ in the cyano $C_1$-$C_4$ alkyl group represent the chain length of the alkyl, for example $CH_2CN$, $CH_2CH_2CN$, $CH_2CH_2CH_2CN$, $CH_2CH_2CH_2CH_2CN$, $CH(CH_3)CN$, $CH(CH_2CH_3)CN$, $CH(CH_2CH_2CH_3)CN$, $C(CH_3)(CH_3)CN$ or $C(CH_3)(CH_2CH_3)CN$.

Insecticide: a substance that has insecticidal effect on pests.

Animal parasite control agent: refers to an active compound that may effectively reduce the incidence of various parasites in animals infected by parasites. The "control" means that the active compound may effectively kill parasites, inhibit their growth or reproduction.

SYNTHESIS EXAMPLES

According to the synthetic route described above, by using different starting material compounds, the compounds represented by the general formula I, general formula II and general formula III of this disclosure may be prepared separately, which are further specifically described as follows.

Example 1: Preparation of Intermediate Compound II.1

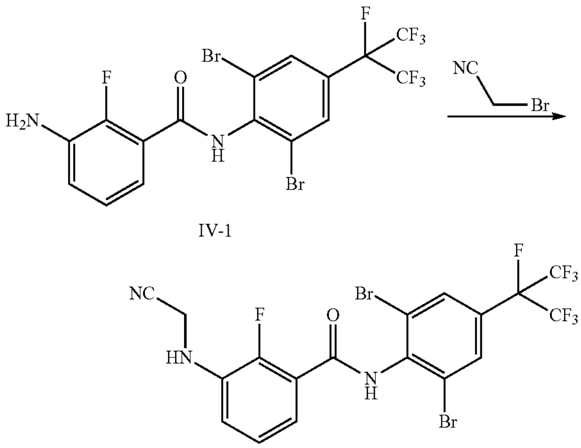

IV-1

II.1

1.00 g (1.80 mmol) of N-(2,6-dibromo-4-heptafluoroisopropylphenyl)-2-fluoro-3-aminobenzamide (intermediate IV-1, prepared by referring to the method reported in WO2011093415 or WO2010018714), 0.37 g (2.68 mmol) of potassium carbonate, 0.27 g (1.80 mmol) of sodium iodide and 0.26 g (2.19 mmol) of bromoacetonitrile were added into 30 ml of DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.50 g of a white solid, which was the intermediate II.1. The NMR and MS data of the intermediate II.1 are as follows:

$^1$H NMR (600 MHz, Chloroform-d) δ 8.11 (d, 1H), 7.88 (s, 2H), 7.64-7.58 (m, 1H), 7.29 (t, 1H), 7.05 (td, 1H), 4.52-4.44 (br, 1H), 4.24 (d, 2H). LC-MS(m/z, ESI): 594.01 $(M+H)^+$.

Example 2: Preparation of Intermediate Compound II.2

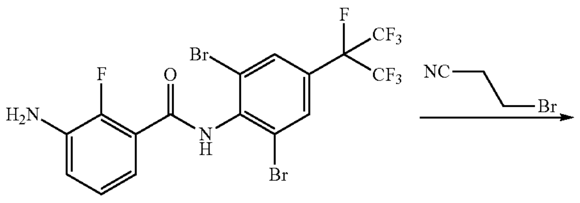

IV-1

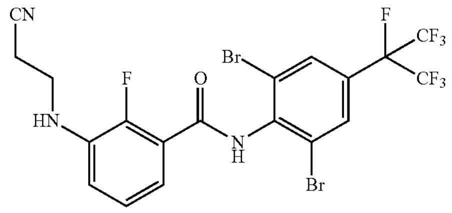

II.2

1.50 g (2.70 mmol) of N-(2,6-dibromo-4-heptafluoroisopropylphenyl)-2-fluoro-3-aminobenzamide (intermediate IV-1), 0.56 g (4.05 mmol) of potassium carbonate, 0.41 g (2.74 mmol) of sodium iodide and 0.43 g (3.21 mmol) of bromopropionitrile were added to 50 ml of DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.25 g of a white solid, which was the intermediate II.2. The NMR and MS data of the intermediate II.2 are as follows:

$^1$H NMR (600 MHz, Chloroform-d) δ 8.16 (d, 1H), 7.87 (s, 2H), 7.52-7.46 (m, 1H), 7.20 (t, 1H), 6.90 (td, 1H), 4.46-4.40 (m, 1H), 3.66-3.60 (m, 2H), 2.72 (t, 2H). LC-MS (m/z, ESI): 608.01 $(M+H)^+$.

Example 3: Preparation of Intermediate Compound II.3

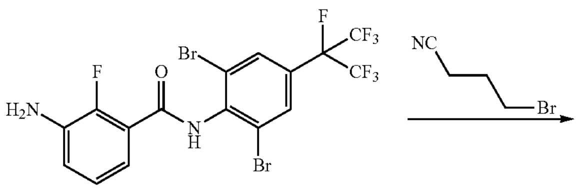

IV-1

-continued

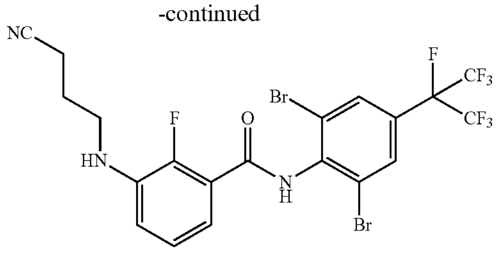

II.3

1.00 g (1.80 mmol) of N-(2,6-dibromo-4-heptafluoroisopropylphenyl)-2-fluoro-3-aminobenzamide (intermediate IV-1), 0.37 g (2.68 mmol) of potassium carbonate, 0.27 g (1.80 mmol) of sodium iodide and 0.32 g (2.16 mmol) of bromobutyronitrile were added to 30 ml DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.12 g of a white solid, which was the intermediate II.3. The NMR and MS data of Intermediate II.3 are as follows:

$^1$H NMR (600 MHz, Chloroform-d) δ 8.16 (d, 1H), 7.87 (s, 2H), 7.46-7.42 (m, 1H), 7.18 (t, 1H), 6.94 (td, 1H), 4.17-4.10 (m, 1H), 3.43 (q, 2H), 2.54 (t, 2H), 2.08-2.02 (m, 2H). LC-MS (m/z, ESI): 622.03 $(M+H)^+$.

Example 4: Preparation of Intermediate Compound II.4

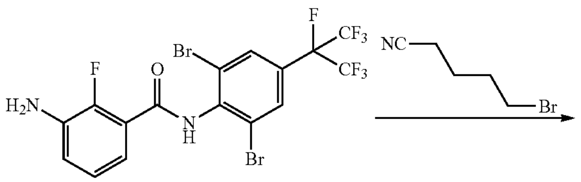

IV-1

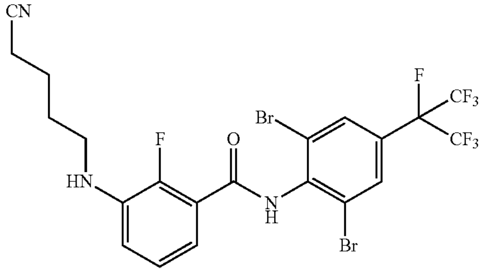

II.4

1.00 g (1.80 mmol) of N-(2,6-dibromo-4-heptafluoroisopropylphenyl)-2-fluoro-3-aminobenzamide (intermediate IV-1), 0.37 g (2.68 mmol) of potassium carbonate, 0.27 g (1.80 mmol) of sodium iodide and 0.35 g (2.16 mmol) of bromovaleronitrile were added to 30 ml DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.11 g of a white solid, which was the intermediate II.4. The NMR and MS data of the intermediate II.4 are as follows:

$^1$H NMR (600 MHz, Chloroform-d) δ 8.19 (d, 1H), 7.87 (s, 2H), 7.40 (t, 1H), 7.16 (t, 1H), 6.90 (t, 1H), 4.07 (s, 1H), 3.31-3.23 (m, 2H), 2.44 (t, 2H), 1.91-1.78 (m, 4H). LC-MS (m/z, ESI): 636.10 $(M+H)^+$.

Example 5: Preparation of Intermediate Compound II.5

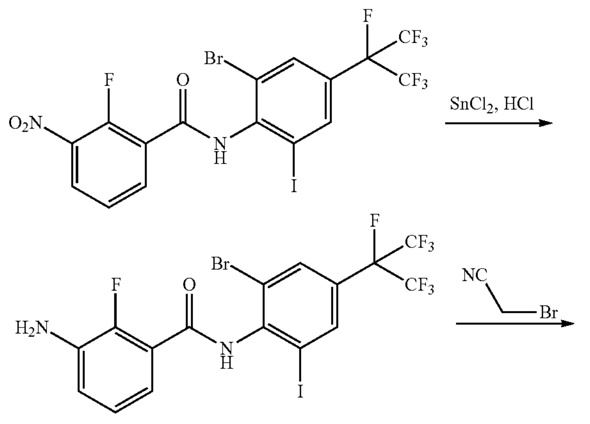

IV-2

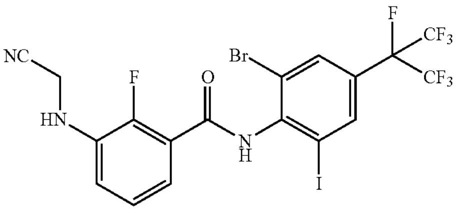

II.1

10 g of N-(2-bromo-6-iodo-4-heptafluoroisopropylphenyl)-2-fluoro-3-nitrobenzamide (prepared by referring to the method reported in CN109206335A), 15 g of anhydrous stannous chloride, 200 ml of 1,4-dioxane and 8 ml of concentrated hydrochloric acid were added, and then heated to 60V while being stirred for reaction. After the reaction was completed under monitoring by TLC, the organic solvent was distilled off under reduced pressure. 500 ml of ethyl acetate were added, and then an appropriate amount of saturated sodium hydroxide aqueous solution was added to adjust the pH=10. After thorough stirring, celite was used to filter out the precipitated insoluble matter. After the filtrate was extracted with ethyl acetate and water, the organic layer was dried over anhydrous magnesium sulfate, filtered and concentrated under reduced pressure to obtain a beige solid. The crude product was purified by column chromatography to obtain 7.91 g of N-(2-bromo-6-iodo-4-heptafluoroisopropylphenyl)-2-fluoro-3-aminobenzamide (intermediate IV-2).

1.00 g (1.66 mmol) of N-(2-bromo-6-iodo-4-heptafluoroisopropylphenyl)-2-fluoro-3-aminobenzamide (intermediate IV-2), 0.34 g (2.46 mmol) of potassium carbonate, 0.25 g (1.67 mmol) of sodium iodide and 0.24 g (2.00 mmol) of bromoacetonitrile were added to 30 ml of DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.43 g of a white solid, which was the intermediate II.5. The NMR and MS data of the intermediate II.5 are as follows:

$^1$H NMR (600 MHz, Chloroform-d) δ 8.12 (d, 1H), 8.08 (d, 1H), 7.90 (d, 1H), 7.61 (t, 1H), 7.29 (t, 1H), 7.05 (td, 1H), 4.54-4.47 (br, 1H), 4.24 (d, 2H). LC-MS (m/z, ESI): 642.05 $(M+H)^+$.

Example 6: Preparation of Intermediate Compound II.6

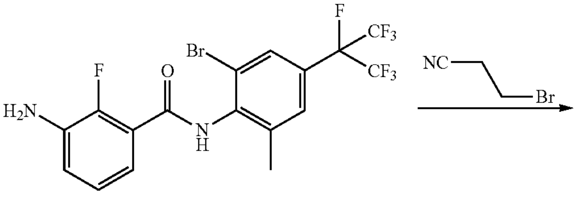

IV-2

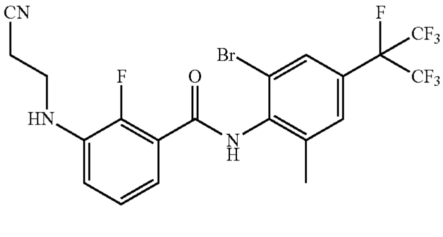

II.6

2.00 g (3.32 mmol) of N-(2-bromo-6-iodo-4-heptafluoroisopropylphenyl)-2-fluoro-3-aminobenzamide (intermediate IV-2), 0.69 g (4.99 mmol) of potassium carbonate, 0.50 g (3.34 mmol) of sodium iodide and 0.53 g (3.96 mmol) of bromopropionitrile were added to 60 ml of DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.26 g of a white solid, which was the intermediate II.6. The NMR and MS data of Intermediate II.6 are as follows:

$^1$H NMR (600 MHz, Chloroform-d) δ 8.17 (d, 1H), 8.08 (d, 1H), 7.90 (d, 1H), 7.50 (t, 1H), 7.20 (t, 1H), 6.91 (td, 1H), 4.48-4.40 (m, 1H), 3.63 (q, 2H), 2.72 (t, 2H). LC-MS (m/z, ESI): 656.07 $(M+H)^+$.

Example 7: Preparation of Intermediate Compound II.9

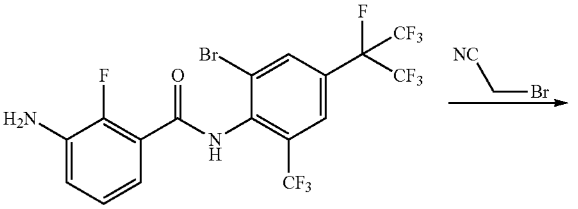

IV-3

-continued

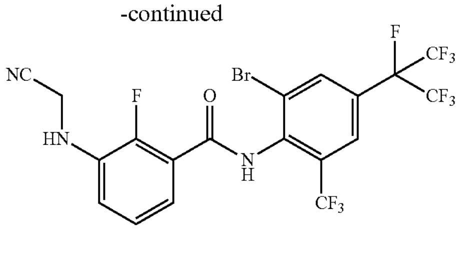

II.9

2.00 g (3.67 mmol) of N-(2-bromo-6-trifluoromethyl-4-heptafluoroisopropylphenyl)-2-fluoro-3-aminobenzamide (intermediate IV-3, prepared by referring to the method reported in WO2011093415 or WO2010018714), 0.76 g (5.50 mmol) of potassium carbonate, 0.56 g (3.74 mmol) of sodium iodide and 0.53 g (4.42 mmol) of bromoacetonitrile were added into 60 ml of DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.78 g of a white solid, which was the intermediate II.9. The NMR and MS data of Intermediate II.9 are as follows:

$^1$H NMR (600 MHz, Chloroform-d) δ 8.18 (d, 1H), 8.16-8.13 (m, 1H), 7.94-7.90 (m, 1H), 7.63-7.55 (m, 1H), 7.29 (t, 1H), 7.05 (td, 1H), 4.52-4.45 (m, 1H), 4.24 (d, 2H). LC-MS (m/z, ESI): 584.04 $(M+H)^+$.

Example 8: Preparation of Intermediate Compound II.10

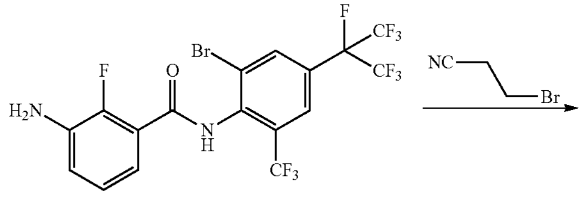

IV-3

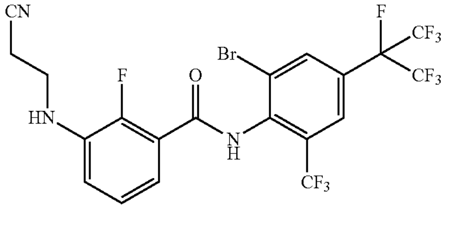

II.10

2.00 (3.67 mmol) of N-(2-bromo-6-trifluoromethyl-4-heptafluoroisopropylphenyl)-2-fluoro-3-aminobenzamide (intermediate IV-3), 0.76 g (5.50 mmol) of potassium carbonate, 0.55 g (3.67 mmol) of sodium iodide and 0.59 g (4.40 mmol) of bromopropionitrile were added to 60 ml of DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.22 g of a white solid, which was the intermediate II.10. The NMR and MS data of Intermediate II.10 are as follows:

$^1$H NMR (600 MHz, Chloroform-d) δ 8.22 (d, 1H), 8.16-8.13 (m, 1H), 7.93-7.90 (m, 1H), 7.50-7.45 (m, 1H), 7.20 (t, 1H), 6.91 (td, 1H), 4.46-4.38 (m, 1H), 3.63 (q, 2H), 2.72 (t, 2H). LC-MS (m/z, ESI): 598.05 $(M+H)^+$.

Example 9: Preparation of Intermediate Compound II.11

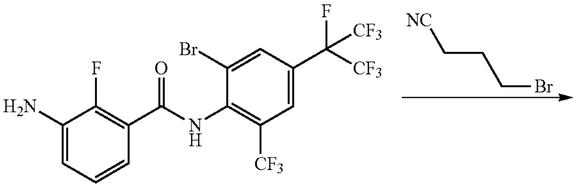

IV-3

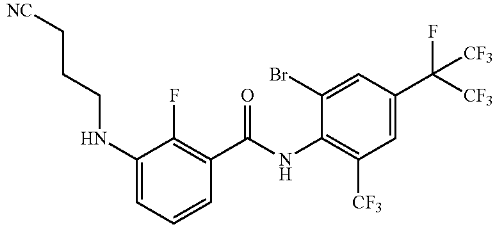

II.11

1.30 (2.39 mmol) of N-(2-bromo-6-trifluoromethyl-4-heptafluoroisopropylphenyl)-2-fluoro-3-aminobenzamide (intermediate IV-3), 0.49 g (3.55 mmol) of potassium carbonate, 0.36 g (2.40 mmol) of sodium iodide and 0.46 g (3.13 mmol) of bromobutyronitrile were added to 40 ml of DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.19 g of a white solid, which was the intermediate II.11. The NMR and MS data of Intermediate II.11 are as follows:

$^1$H NMR (600 MHz, Chloroform-d) δ 8.22 (d, 1H), 8.15-8.13 (m, 1H), 7.92-7.90 (m, 1H), 7.46-7.40 (m, 1H), 7.18 (t, 1H), 6.94 (td, 1H), 4.17-4.09 (m, 1H), 3.43 (q, 2H), 2.54 (t, 2H), 2.08-2.02 (m, 2H). LC-MS (m/z, ESI): 612.06 $(M+H)^+$.

Example 10: Preparation of Intermediate Compound II.12

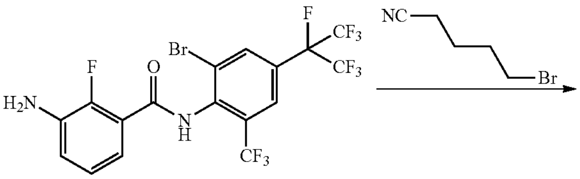

IV-3

-continued

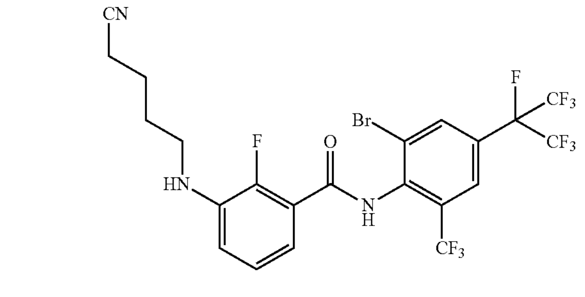

II.12

1.65 (3.03 mmol) of N-(2-bromo-6-trifluoromethyl-4-heptafluoroisopropylphenyl)-2-fluoro-3-aminobenzamide (intermediate IV-3), 0.62 g (4.50 mmol) of potassium carbonate, 0.46 g (3.07 mmol) of sodium iodide, and 0.61 g (3.79 mmol) of bromovaleronitrile were added to 50 ml of DMF, which was then heated to 100° C. for reaction. After the reaction was completed under monitoring by TLC, water and ethyl acetate were added for extraction, where the solvent in the organic phase was removed under reduced pressure, and the residue was purified by column chromatography to obtain 0.21 g of a white solid, which was the intermediate II.12. The NMR and MS data of Intermediate II.12 are as follows:

$^1$H NMR (600 MHz, Chloroform-d) δ 8.23 (d, 1H), 8.14 (d, 1H), 7.91 (d, 1H), 7.42-7.37 (m, 1H), 7.17 (t, 1H), 6.91 (td, 1H), 4.13-3.98 (m, 1H), 3.28 (t, 2H), 2.45 (t, 2H), 1.93-1.80 (m, 4H). LC-MS (m/z, ESI): 626.05 $(M+H)^+$.

Example 11: Preparation of Intermediate Compound II.13

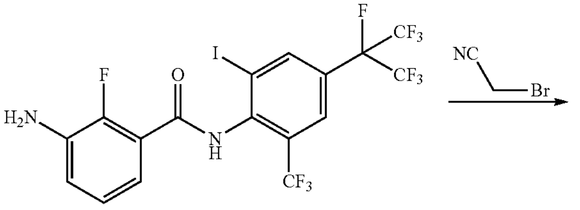

IV-4

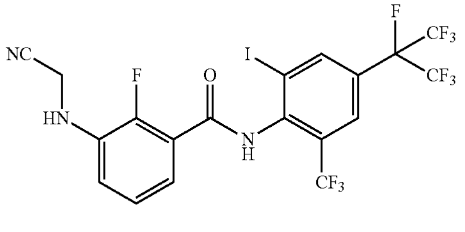

II.13

According to the method described in Example 7, the intermediate compound IV-4 (prepared by referring to the method reported in WO2011093415 or WO2010018714) was reacted with bromoacetonitrile to prepare the intermediate compound II.13 (white solid). The NMR and MS data of the intermediate compound II.13 are as follows:

$^1$H NMR (600 MHz, Chloroform-d) δ 8.37-8.34 (m, 1H), 8.22 (d, 1H), 7.96-7.93 (m, 1H), 7.64-7.57 (m, 1H), 7.29 (t, 1H), 7.05 (td, 1H), 4.52-4.45 (m, 1H), 4.25 (d, 2H). LC-MS (m/z, ESI): 631.99 $(M+H)^+$.

Example 12: Preparation of Intermediate Compound II.14

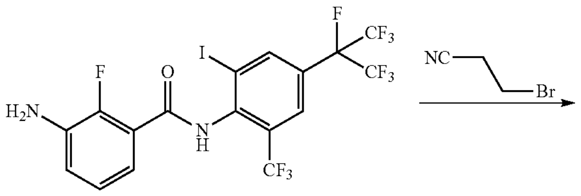

IV-4

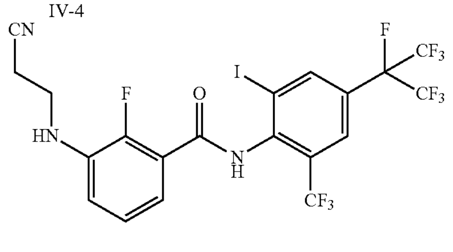

II.14

According to the method described in Example 8, the intermediate compound IV-4 was reacted with bromopropionitrile to prepare the intermediate compound II.14 (white solid). The NMR and MS data of the intermediate compound II.14 are as follows:

$^1$H NMR (600 MHz, Chloroform-d) δ 8.36 (d, 1H), 8.26 (d, 1H), 7.94 (d, 1H), 7.51-7.46 (m, 1H), 7.21 (t, 1H), 6.92 (td, 1H), 4.47-4.39 (m, 1H), 3.64 (q, 2H), 2.72 (t, 2H). LC-MS (m/z, ESI): 646.02 $(M+H)^+$.

Example 13: Preparation of Intermediate Compound II.15

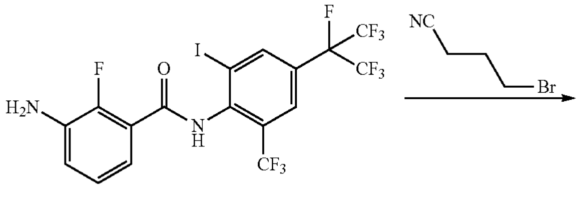

IV-4

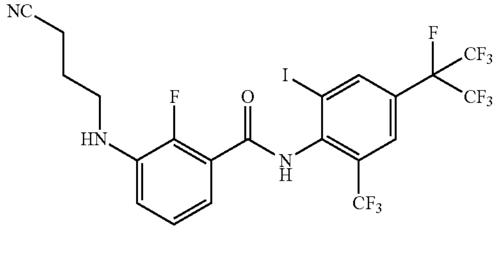

II.15

According to the method described in Example 9, the intermediate compound IV-4 was reacted with bromobutyronitrile to prepare the intermediate compound II.15 (white solid). The NMR and MS data of the intermediate compound II.15 are as follows:

$^1$H NMR (600 MHz, Chloroform-d) δ 8.36-8.34 (m, 1H), 8.27 (d, 1H), 7.95-7.92 (m, 1H), 7.45-7.40 (m, 1H), 7.18 (td, 1H), 6.94 (td, 1H), 4.18-4.11 (br s, 1H), 3.43 (q, 2H), 2.54 (t, 2H), 2.08-2.02 (m, 2H). LC-MS (m/z, ESI): 682.24 $(M+Na)^+$.

Example 14: Preparation of Intermediate Compound II.16

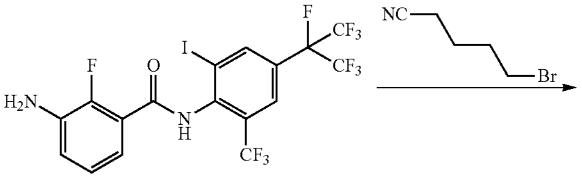

IV-4

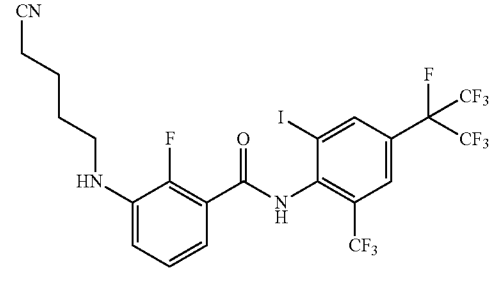

II.16

According to the method described in Example 10, the intermediate compound IV-4 was reacted with bromovaleronitrile to prepare the intermediate compound II.16 (white solid). The NMR and MS data of the intermediate compound II.16 are as follows:

$^1$H NMR (600 MHz, Chloroform-d) δ 8.35 (d, 1H), 8.28 (d, 1H), 7.93 (d, 1H), 7.43-7.38 (m, 1H), 7.17 (t, 1H), 6.91 (td, 1H), 4.22-3.90 (br s, 1H), 3.28 (t, 2H), 2.45 (t, 2H), 1.92-1.81 (m, 4H). LC-MS (m/z, ESI): 696.26 $(M+Na)^+$.

Example 15: Preparation of Compound 1

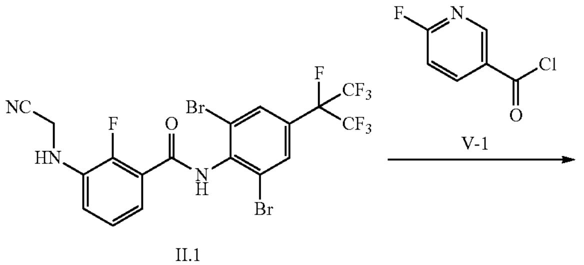

II.1

-continued

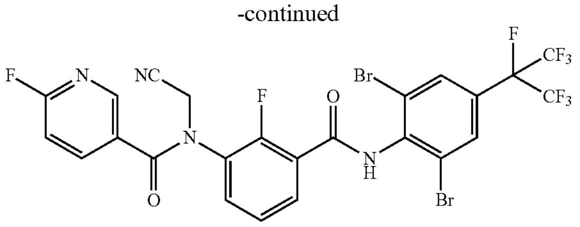

1

0.30 g (0.51 mmol) of the intermediate II.1 and 0.12 g (0.76 mmol) of the intermediate V-1 were added to 20 mL of toluene, which was then heated to reflux. After the reaction was completed under monitoring by TLC, the solvent was removed under reduced pressure, and the residue was purified by column chromatography to obtain 0.26 g of a white solid, which was the compound 1. The NMR and MS data of the compound 1 are as follows:

$^1$H NMR (600 MHz, Chloroform-d) δ 8.24 (d, 1H), 8.16 (t, 1H), 7.98 (d, 1H), 7.91-7.85 (m, 3H), 7.54 (td, 1H), 7.39 (t, 1H), 6.87 (dd, 1H), 4.95 (br s, 1H), 4.64 (br s, 1H). LC-MS (m/z, ESI): 717.04 $(M+H)^+$.

Example 16: Preparation of Compound 2

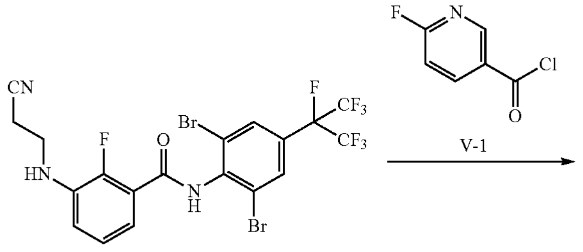

II.2

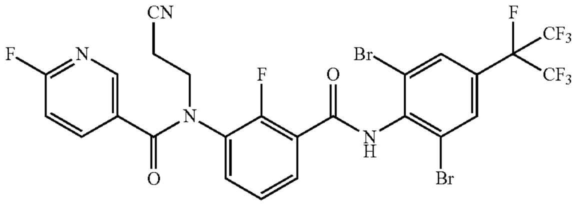

2

0.30 g (0.49 mmol) of the intermediate II.2 and 0.12 g (0.75 mmol) of the intermediate V-1 were added to 20 mL of toluene, which was then heated to reflux. After the reaction was completed under monitoring by TLC, the solvent was removed under reduced pressure, and the residue was purified by column chromatography to obtain 0.24 g of a yellow solid, which was the compound 2. The NMR and MS data of the compound 2 are as follows:

$^1$H NMR (600 MHz, Chloroform-d) δ 8.23 (d, 1H), 8.06 (t, 1H), 7.93 (d, 1H), 7.88-7.80 (m, 3H), 7.64 (td, 1H), 7.39 (t, 1H), 6.83 (dd, 1H), 4.24-4.10 (m, 2H), 2.99 (br, 1H), 2.88 (br, 1H). LC-MS (m/z, ESI): 731.07 $(M+H)^+$.

Example 17: Preparation of Compound 3

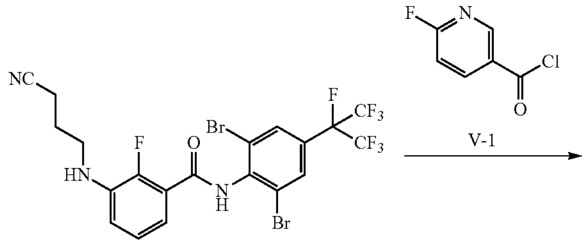

II.3

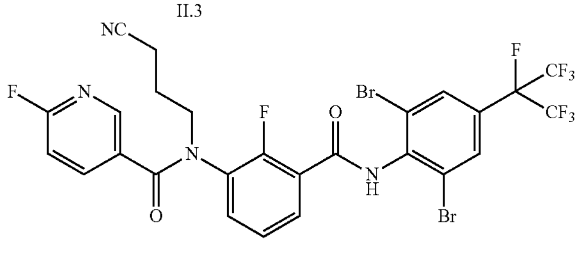

3

0.30 g (0.48 mmol) of the intermediate II.3 and 0.12 g (0.76 mmol) of the intermediate V-1 were added to 20 mL of toluene, which was then heated to reflux. After the reaction was completed under monitoring by TLC, the solvent was removed under reduced pressure, and the residue was purified by column chromatography to obtain 0.27 g of a yellow solid, which was the compound 3. The NMR and MS data of the compound 3 are as follows: $^1$H NMR (600 MHz, Chloroform-d) δ 8.19 (d, 1H), 8.08 (t, 1H), 7.94 (d, 1H), 7.86 (s, 2H), 7.81 (td, 1H), 7.51 (td, 1H), 7.36 (t, 1H), 6.81 (dd, 1H), 4.16-3.98 (m, 2H), 2.54 (t, 2H), 2.16-2.01 (m, 2H). LC-MS (m/z, ESI): 745.11 $(M+H)^+$.

Example 18: Preparation of Compound 4

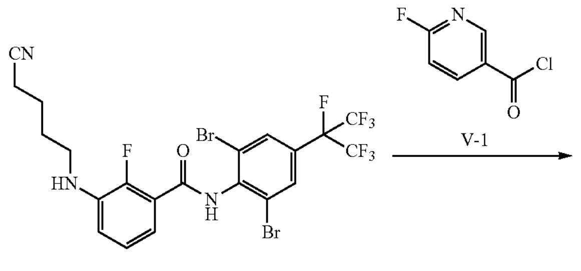

II.4

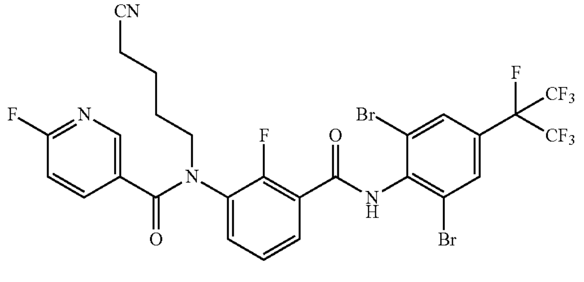

4

0.30 g (0.47 mmol) of the intermediate II.4 and 0.11 g (0.69 mmol) of the intermediate V-1 were added to 20 mL of toluene, which was then heated to reflux. After the reaction was completed under monitoring by TLC, the solvent was removed under reduced pressure, and the residue was purified by column chromatography to obtain 0.25 g of a yellow solid, which was the compound 4. The NMR and MS data of the compound 4 are as follows:

$^1$H NMR (600 MHz, Chloroform-d) δ 8.18 (s, 1H), 8.10-8.00 (m, 2H), 7.85 (s, 2H), 7.78 (t, 1H), 7.49 (t, 1H), 7.36 (t, 1H), 6.80 (d, 1H), 4.25-4.10 (br, 1H), 3.91-3.80 (br, 1H), 2.54-2.36 (m, 2H), 1.90-1.76 (m, 4H). LC-MS (m/z, ESI): 759.13 $(M+H)^+$.

Example 19: Preparation of Compound 5

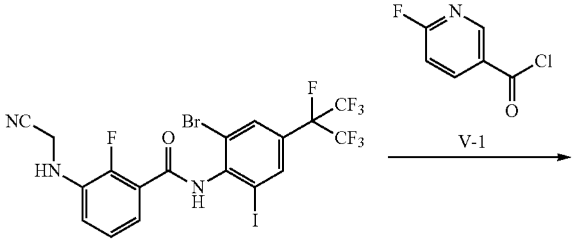

II.5

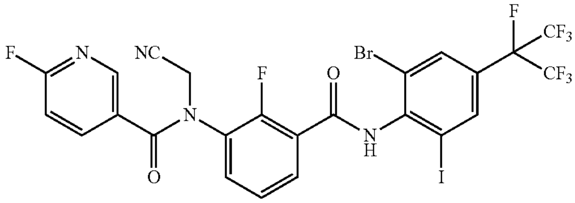

5

0.30 g (0.47 mmol) of the intermediate II.5 and 0.11 g (0.69 mmol) of the intermediate V-1 were added to 20 mL of toluene, which was then heated to reflux. After the reaction was completed under monitoring by TLC, the solvent was removed under reduced pressure, and the residue was purified by column chromatography to obtain 0.23 g of a white solid, which was the compound 5. The NMR and MS data of the compound 5 are as follows:

$^1$H NMR (600 MHz, Chloroform-d) δ 8.25 (d, 1H), 8.17 (t, 1H), 8.07 (d, 1H), 7.97 (d, 1H), 7.91-7.85 (m, 2H), 7.56 (td, 1H), 7.41 (t, 1H), 6.86 (dd, 1H), 4.94 (br s, 1H), 4.65 (br s, 1H). LC-MS (m/z, ESI): 765.05 $(M+H)^+$.

Example 20: Preparation of Compound 6

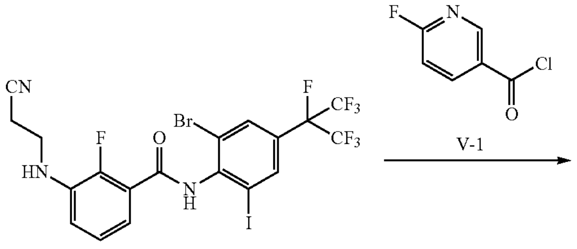

II.6

-continued

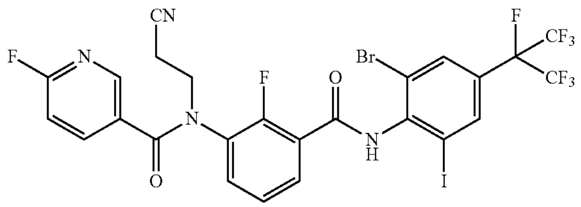

6

0.50 g (0.76 mmol) of the intermediate II.6 and 0.18 g (1.13 mmol) of the intermediate V-1 were added to 30 mL of toluene, which was then heated to reflux. After the reaction was completed under monitoring by TLC, the solvent was removed under reduced pressure, and the residue was purified by column chromatography to obtain 0.41 g of a white solid, which was the compound 6. The NMR and MS data of the compound 6 are as follows:

$^1$H NMR (600 MHz, Chloroform-d) δ 8.25 (d, 1H), 8.09 (t, 1H), 8.06 (d, 1H), 7.91 (d, 1H), 7.88 (d, 1H), 7.83 (td, 1H), 7.67 (td, 1H), 7.41 (t, 1H), 6.83 (dd, 1H), 4.22-4.13 (m, 2H), 3.08-2.96 (br, 1H), 2.94-2.81 (br, 1H). LC-MS (m/z, ESI): 778.96 $(M+H)^+$.

Example 21: Preparation of Compound 9

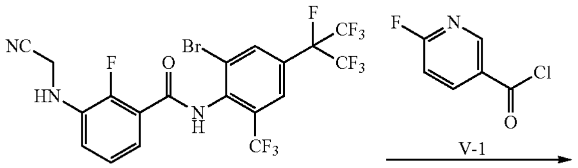

II.9

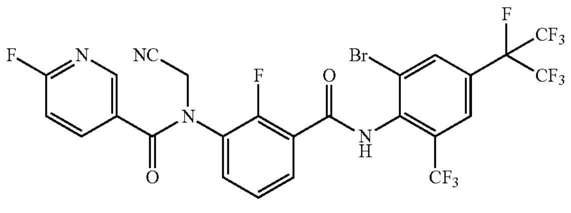

9

0.50 g (0.86 mmol) of the intermediate II.9 and 0.21 g (1.32 mmol) of the intermediate V-1 were added to 30 mL of toluene, which was then heated to reflux. After the reaction was completed under monitoring by TLC, the solvent was removed under reduced pressure, and the residue was purified by column chromatography to obtain 0.47 g of a white solid, which was the compound 9. The NMR and MS data of the compound 9 are as follows:

$^1$H NMR (600 MHz, Chloroform-d) δ 8.21 (d, 1H), 8.17-8.12 (m, 2H), 8.01 (d, 1H), 7.92-7.85 (m, 2H), 7.57 (td, 1H), 7.41 (t, 1H), 6.88 (dd, 1H), 4.95 (br s, 1H), 4.63 (br s, 1H). LC-MS (m/z, ESI): 707.08 $(M+H)^+$.

Example 22: Preparation of Compound 10

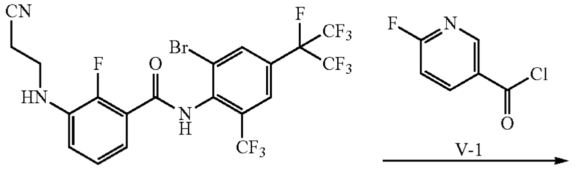

II.10

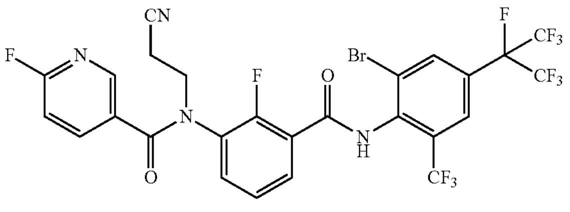

10

0.50 g (0.84 mmol) of the intermediate II.10 and 0.20 g (1.25 mmol) of the intermediate V-1 were added to 30 mL of toluene, which was then heated to reflux. After the reaction was completed under monitoring by TLC, the solvent was removed under reduced pressure, and the residue was purified by column chromatography to obtain 0.42 g of a white solid, which was the compound 10. The NMR and MS data of the compound 10 are as follows:

$^1$H NMR (600 MHz, Chloroform-d) δ 8.24-8.19 (m, 1H), 8.14-8.11 (m, 1H), 8.05 (t, 1H), 7.94 (d, 1H), 7.90 (d, 1H), 7.87-7.81 (m, 1H), 7.68 (td, 1H), 7.41 (t, 1H), 6.85 (dd, 1H), 4.17 (t, 2H), 3.08-2.95 (br, 1H), 2.94-2.84 (br, 1H). LC-MS (m/z, ESI): 721.08 $(M+H)^+$.

Example 23: Preparation of Compound 11

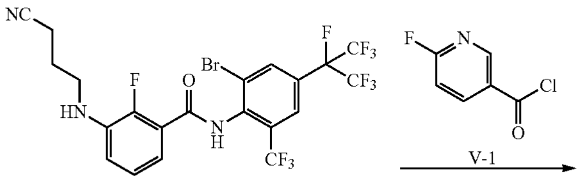

II.11

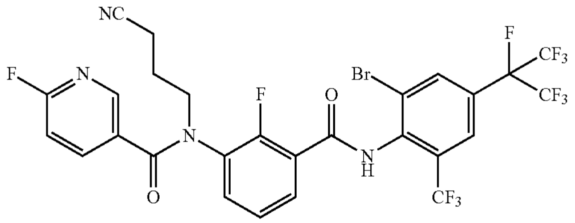

11

According to the method described in Example 21, the intermediate compound II.11 was reacted with the intermediate compound V-1 to prepare the compound 11 (yellow solid). The NMR and MS data of the compound 11 are as follows:

$^1$H NMR (600 MHz, Chloroform-d) δ 8.16 (s, 1H), 8.14-8.12 (m, 1H), 8.09-8.04 (m, 1H), 7.98 (d, 1H), 7.92-7.89 (m, 1H), 7.82 (td, 1H), 7.54 (td, 1H), 7.37 (t, 1H), 6.83

(dd, 1H), 4.19-3.96 (m, 2H), 2.54 (t, 2H), 2.17-2.02 (m, 2H). LC-MS (m/z, ESI): 735.21 $(M+H)^+$.

Example 24: Preparation of Compound 12

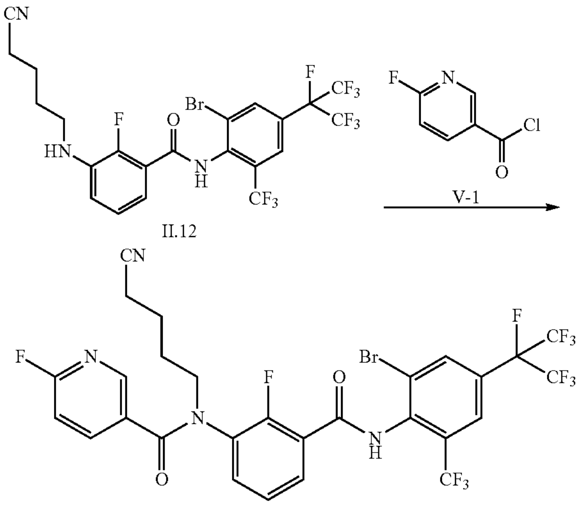

II.12

12

According to the method described in Example 21, the intermediate compound II.12 was reacted with the intermediate V-1 to prepare the compound 12 (yellow solid). The NMR and MS data of the compound 12 are as follows:

$^1$H NMR (600 MHz, Chloroform-d) δ 8.19-8.09 (m, 3H), 8.04-7.99 (m, 1H), 7.91-7.88 (m, 1H), 7.82-7.77 (m, 1H), 7.51 (td, 1H), 7.37 (t, 1H), 6.82 (dd, 1H), 4.21 (br s, 1H), 3.84 (br s, 1H), 2.55-2.36 (m, 2H), 1.91-1.75 (m, 4H). LC-MS (m/z, ESI): 747.37 $(M-H)^-$.

Example 25: Preparation of Compound 13

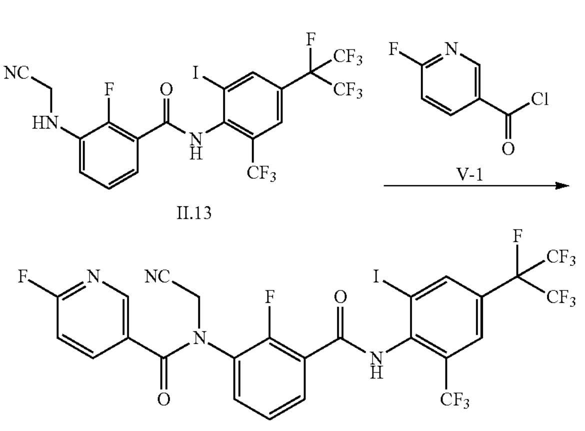

II.13

13

According to the method described in Example 21, the intermediate compound II.13 was reacted with the intermediate V-1 to prepare the compound 13 (white solid). The NMR and MS data of the compound 13 are as follows:

$^1$H NMR (600 MHz, Chloroform-d) δ 8.34 (d, 1H), 8.22 (d, 1H), 8.19-8.13 (m, 1H), 8.03 (d, 1H), 7.93 (d, 1H), 7.91-7.85 (m, 1H), 7.59 (td, 1H), 7.42 (t, 1H), 6.87 (dd, 1H), 4.97 (br s, 1H), 4.64 (br s, 1H). LC-MS (m/z, ESI): 755.01 $(M+H)^+$.

Example 26: Preparation of Compound 14

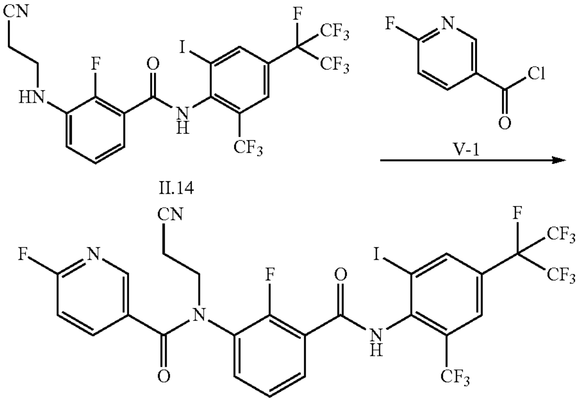

II.14

14

According to the method described in Example 21, the intermediate compound II.14 was reacted with the intermediate V-1 to prepare the compound 14 (white solid). The NMR and MS data of the compound 14 are as follows:

$^1$H NMR (600 MHz, Chloroform-d) δ 8.33 (d, 1H), 8.21 (d, 1H), 8.06 (td, 1H), 8.00 (d, 1H), 7.93-7.90 (m, 1H), 7.86-7.81 (m, 1H), 7.69 (td, 1H), 7.42 (t, 1H), 6.84 (dd, 1H), 4.16 (t, 2H), 3.08-2.96 (br, 1H), 2.94-2.82 (br, 1H). LC-MS (m/z, ESI): 767.36 $(M-H)^-$.

Example 27: Preparation of Compound 15

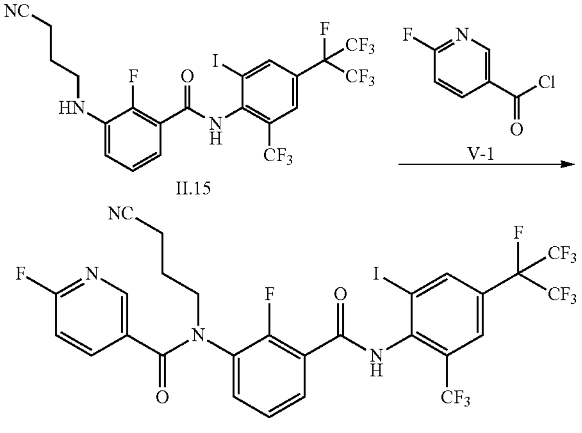

II.15

15

According to the method described in Example 21, the intermediate compound II.15 was reacted with the intermediate V-1 to prepare the compound 15 (yellow solid). The NMR and MS data of the compound 15 are as follows:

$^1$H NMR (600 MHz, Chloroform-d) δ 8.34 (d, 1H), 8.17 (d, 1H), 8.10-7.98 (m, 2H), 7.93-7.91 (m, 1H), 7.82 (td, 1H), 7.55 (td, 1H), 7.41-7.36 (m, 1H), 6.82 (dd, 1H), 4.19-3.96 (m, 2H), 2.55 (t, 2H), 2.19-2.02 (m, 2H). LC-MS (m/z, ESI): 805.30 $(M+Na)^+$.

Example 28: Preparation of Compound 16

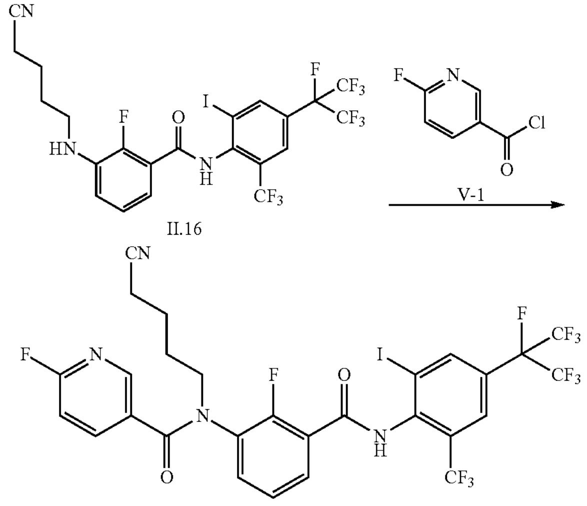

II.16

16

According to the method described in Example 21, the intermediate compound II.16 was reacted with the intermediate V-1 to prepare the compound 16 (yellow oily matter). The NMR and MS data of the compound 16 are as follows:

$^1$H NMR (600 MHz, Chloroform-d) δ 8.33 (d, 1H), 8.24-8.11 (m, 2H), 8.05-7.99 (m, 1H), 7.94-7.90 (m, 1H), 7.83-7.75 (m, 1H), 7.53 (td, 1H), 7.38 (t, 1H), 6.81 (d, 1H), 4.23 (br s, 1H), 3.84 (br s, 1H), 2.56-2.36 (m, 2H), 1.94-1.75 (m, 4H). LC-MS (m/z, ESI): 819.33 $(M+Na)^+$.

Example 29: Preparation of Compound 17

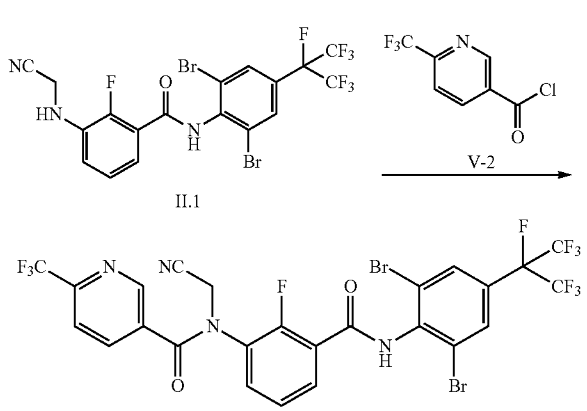

II.1

17

According to the method described in Example 15, the intermediate compound II.1 was reacted with the intermediate V-2 to prepare the compound 17 (white solid). The NMR and MS data of the compound 17 are as follows:

$^1$H NMR (600 MHz, Chloroform-d) δ 8.70 (s, 1H), 8.18 (t, 1H), 7.98-7.90 (m, 2H), 7.87 (s, 2H), 7.63 (d, 1H), 7.57 (td, 1H), 7.41 (t, 1H), 4.99 (d, 1H), 4.66 (d, 1H). LC-MS (m/z, ESI): 767.06 $(M+H)^+$.

Example 30: Preparation of Compound 25

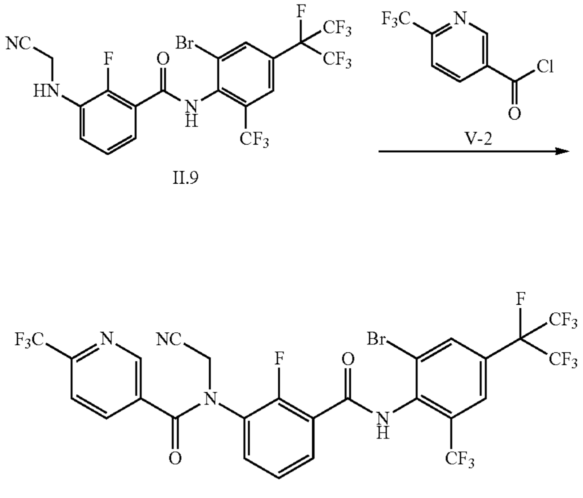

II.9

25

According to the method described in Example 21, the intermediate compound II.9 was reacted with the intermediate V-2 to prepare the compound 25 (yellow solid). The NMR and MS data of the compound 25 are as follows:

$^1$H NMR (600 MHz, Chloroform-d) δ 8.67 (s, 1H), 8.20-8.15 (m, 1H), 8.14 (d, 1H), 7.99-7.93 (m, 2H), 7.92-7.89 (m, 1H), 7.67-7.59 (m, 2H), 7.44 (t, 1H), 4.99 (d, 1H), 4.68 (d, 1H). LC-MS (m/z, ESI): 779.28 $(M+Na)^+$.

Example 31: Preparation of Compound 26

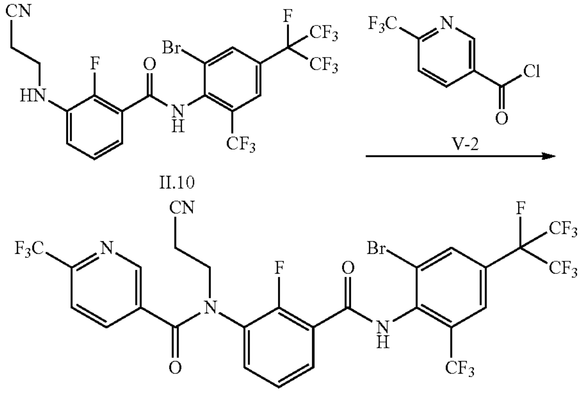

II.10

26

According to the method described in Example 21, the intermediate compound II.10 was reacted with the intermediate V-2 to prepare the compound 26 (yellow solid). The NMR and MS data of the compound 26 are as follows:

$^1$H NMR (600 MHz, Chloroform-d) δ 8.67 (s, 1H), 8.13-8.11 (m, 1H), 8.07 (t, 1H), 7.96-7.87 (m, 3H), 7.71 (td, 1H), 7.60 (d, 1H), 7.43 (t, 1H), 4.25-4.15 (m, 1H), 3.08-2.98 (m, 1H), 2.94-2.84 (m, 1H). LC-MS (m/z, ESI): 793.33 $(M+Na)^+$.

Example 32: Preparation of Compound 27

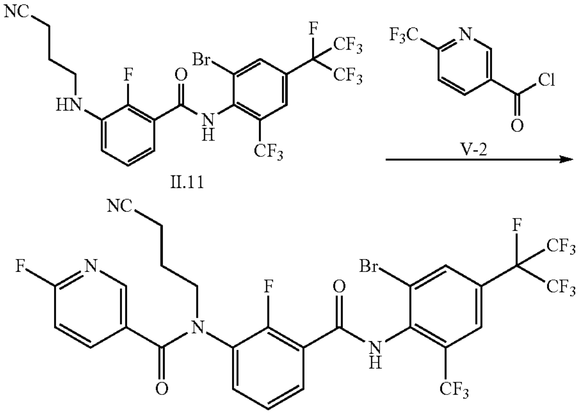

27

According to the method described in Example 21, the intermediate compound II.11 was reacted with the intermediate compound V-2 to prepare the compound 27 (yellow solid). The NMR data of the compound 27 is as follows:

$^1$H NMR (600 MHz, Chloroform-d) δ 8.62 (s, 1H), 8.13 (d, 1H), 8.07 (t, 1H), 7.99-7.93 (m, 1H), 7.91-7.85 (m, 2H), 7.61-7.55 (m, 2H), 7.39 (t, 1H), 4.20-4.11 (m, 1H), 4.09-4.00 (m, 1H), 2.56 (t, 2H), 2.19-2.03 (m, 2H).

Example 33: Preparation of Compound 28

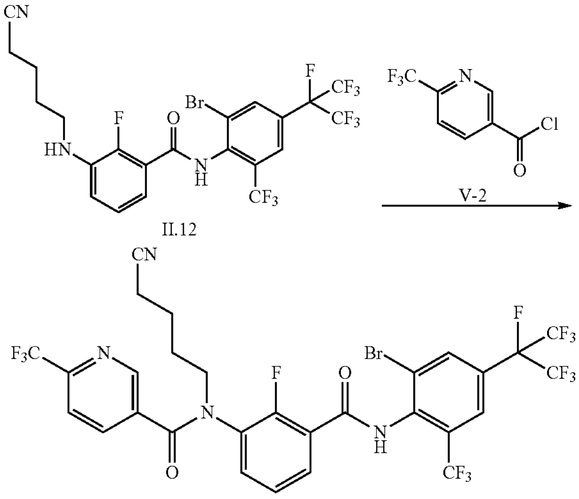

28

According to the method described in Example 21, the intermediate compound II.12 was reacted with the intermediate V-2 to prepare the compound 28 (yellow solid). The NMR and MS data of the compound 28 are as follows:

$^1$H NMR (600 MHz, Chloroform-d) δ 8.62 (s, 1H), 8.15-8.06 (m, 2H), 8.03 (t, 1H), 7.91-7.87 (m, 1H), 7.85 (d, 1H), 7.62-7.50 (m, 2H), 7.39 (t, 1H), 4.33-4.21 (br, 1H), 3.90-3.78 (br, 1H), 2.56-2.37 (m, 2H), 1.92-1.76 (m, 4H). LC-MS (m/z, ESI): 821.36 (M+Na)$^+$.

Example 34: Preparation of Compound 29

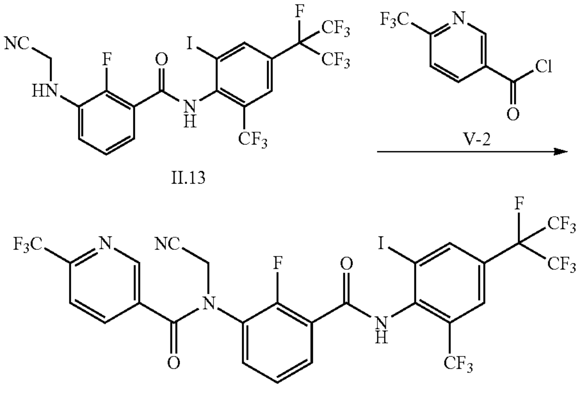

29

According to the method described in Example 21, the intermediate compound II.13 was reacted with the intermediate V-2 to prepare the compound 29 (white solid). The NMR and MS data of the compound 29 are as follows:

$^1$H NMR (600 MHz, Chloroform-d) δ 8.68 (d, 1H), 8.34 (d, 1H), 8.20-8.14 (m, 1H), 8.02 (d, 1H), 7.97-7.91 (m, 2H), 7.67-7.61 (m, 2H), 7.45 (t, 1H), 4.98 (br s, 1H), 4.70 (br s, 1H). LC-MS (m/z, ESI): 827.31 (M+Na)$^+$.

Example 35: Preparation of Compound 32

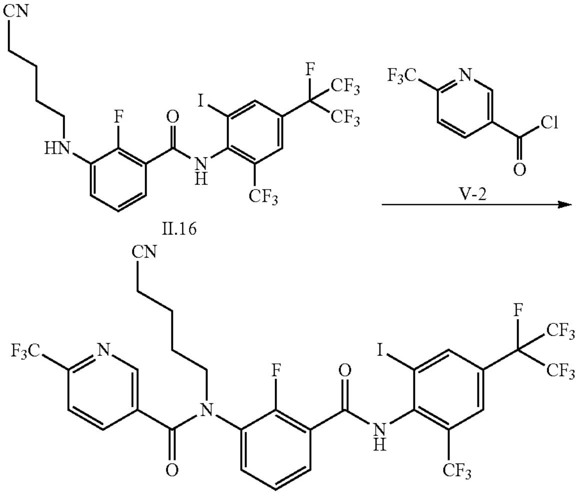

32

According to the method described in Example 21, the intermediate compound II.16 was reacted with the intermediate V-2 to prepare the compound 32 (yellow solid). The NMR and MS data of the compound 32 are as follows:

$^1$H NMR (600 MHz, Chloroform-d) δ 8.63 (s, 1H), 8.34-8.30 (m, 1H), 8.18-8.08 (br, 1H), 8.04 (t, 1H), 7.94-7.88 (m, 1H), 7.84 (d, 1H), 7.61-7.52 (m, 2H), 7.40 (t, 1H), 4.35-4.23 (m, 1H), 3.89-3.78 (m, 1H), 2.56-2.37 (m, 1H), 1.93-1.76 (m, 4H). LC-MS (m/z, ESI): 869.39 (M+Na)$^+$.

With reference to the above examples, other compounds of the general formula I of the present invention can be prepared.

Determination of Biological Activity

Example 36: Determination of Biological Activities Against *Leucania separata, Plutella xylostella*, and *Chilo suppressalis*

The compounds of the invention were determined for the insecticidal activities against several insects. The determination method was as follows:

After being dissolved in a mixed solvent of acetone/methanol (1:1), the test compound was diluted with water containing 0.1% (wt) Tween 80 to the desired concentration.

With *Leucania separata, Plutella xylostella*, and *Chilo suppressalis* as targets, airbrush spray method was used for the determination of the insecticidal activity.

(1) Determination of the Insecticidal Activity Against *Leucania separata*

Determination method: Corn leaves were cut into 2 cm leaf sections, and Airbrush spray treatment was carried out at a pressure of 10 psi (approximately 0.7 kg/$cm^2$) on the front and back sides of each leaf section, with a spray volume of the compound to be tested of 0.5 ml. After drying in the shade, 10 of $3^{rd}$ instar larvae were introduced for each treatment, and each treatment was repeated 3 times. After the treatment, it was placed in an observation room at 25° C. and a relative humidity of 60-70%, and 3 days after the treatment, the number of surviving insects was investigated, and the mortality rate was calculated.

Some of the determination results against Leucania separata were as follows:

At a dose of 0.05 mg/L, 3 days after the treatment, the lethality rates of compounds 1, 2, 3, 4, 5, 6, 9, 10, 11, 12, 13, 14, 15, 16, 17, 25, 26, 27, 28, 29, and 32 against Leucania separata were all 90% or more.

(2) Determination of the Insecticidal Activity Against *Plutella xylostella*

Determination method: Cabbage leaves were punched into leaf discs with a diameter of 2 cm with a puncher, and Airbrush spray treatment was carried out at a pressure of 10 psi (approximately 0.7 kg/$cm^2$) on the front and back sides of each leaf disc, with a spray volume of the compound to be tested of 0.5 ml. After drying in the shade, 10 of 3rd instar larvae were introduced for each treatment, and each treatment was repeated 3 times for. After the treatment, it was placed in an observation room at 25° C. and a relative humidity of 60-70%, and 3 days after the treatment, the number of surviving insects was investigated, and the mortality rate was calculated.

Some of the determination results against *Plutella xylostella* were as follows:

At a dose of 1 mg/L, the lethality rates of compounds 1, 2, 3, 4, 5, 6, 9, 10, 11, 12, 13, 14, 15, 16, 17, 25, 26, 27, 28, 29, and 32 against *Plutella xylostella* were all 90% or more.

At a dose of 0.5 mg/L, the lethality rates of compounds 9, 10, 11, 12, 13, 14, 15, 16, 25, 26, 27, 28, 29, and 32 against *Plutella xylostella* were all 90% or more.

At a dose of 0.05 mg/L, the lethality rates of compounds 9, 10, 11, 12, 13, 14, 15, 16 against *Plutella xylostella* were all 90% or more.

The compounds 2, 10, 26 of this disclosure and the comparative compounds were selected for a parallel comparison test of the insecticidal activity against *Plutella xylostella* (3 days after the treatment), through the same test method as that described above. The results were shown in Table 5:

TABLE 5

Parallel comparison test of the insecticidal activity of the compounds 2, 10, 26 vs. the comparative compounds against *Plutella xylostella*

| | | Lethality rate (%, 3 days after the treatment) | | | |
|---|---|---|---|---|---|
| Compound No. | Structural Formula | 5 mg/L | 1 mg/L | 0.5 mg/L | 0.05 mg/L |
| 2 | 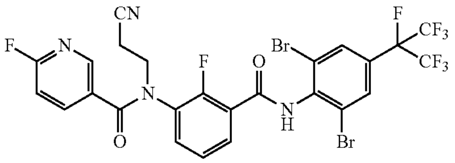 | 100 | 100 | 86.67 | 43.33 |
| 1-1 | 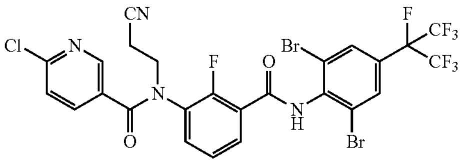 [SMILES: N#CCCN(C(=O)c1ccc(Cl)nc1)c1cccc(C(=O)Nc2c(Br)cc(C(F)(C(F)(F)F)C(F)(F)F)cc2Br)c1F] | 93.33 | 50 | 6.67 | — |
| 1-2 | 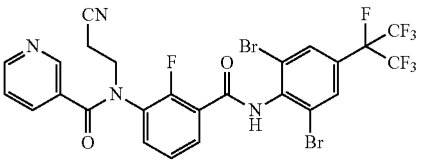 [SMILES: N#CCCN(C(=O)c1cccnc1)c1cccc(C(=O)Nc2c(Br)cc(C(F)(C(F)(F)F)C(F)(F)F)cc2Br)c1F] | 90 | 30 | 0 | — |

TABLE 5-continued
Parallel comparison test of the insecticidal activity of the compounds 2, 10, 26 vs. the comparative compounds against *Plutella xylostella*
| Compound No. | Structural Formula | Lethality rate (%, 3 days after the treatment) 5 mg/L | 1 mg/L | 0.5 mg/L | 0.05 mg/L |
|---|---|---|---|---|---|
| 1-3 | 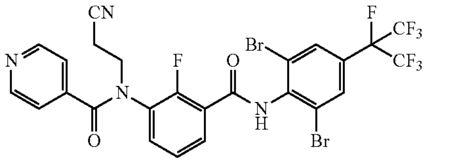 [SMILES: N#CCCN(C(=O)c1ccncc1)c1cccc(C(=O)Nc2c(Br)cc(C(F)(C(F)(F)F)C(F)(F)F)cc2Br)c1F] | 100 | 76.67 | 13.33 | 0 |
| 1-4 | 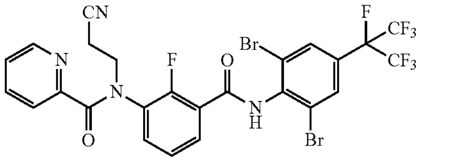 [SMILES: N#CCCN(C(=O)c1ccccn1)c1cccc(C(=O)Nc2c(Br)cc(C(F)(C(F)(F)F)C(F)(F)F)cc2Br)c1F] | 60 | 10 | — | — |
| 1-5 | 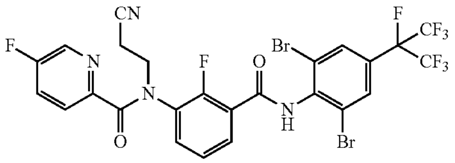 [SMILES: N#CCCN(C(=O)c1ccc(F)cn1)c1cccc(C(=O)Nc2c(Br)cc(C(F)(C(F)(F)F)C(F)(F)F)cc2Br)c1F] | 83.33 | 60 | 33.33 | 0 |
| CK1 | 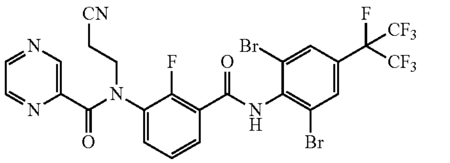 [SMILES: N#CCCN(C(=O)c1cnccn1)c1cccc(C(=O)Nc2c(Br)cc(C(F)(C(F)(F)F)C(F)(F)F)cc2Br)c1F] | 66.67 | 0 | — | — |
| 1-6 | 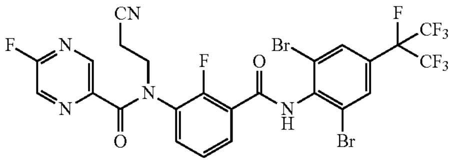 [SMILES: N#CCCN(C(=O)c1cnc(F)cn1)c1cccc(C(=O)Nc2c(Br)cc(C(F)(C(F)(F)F)C(F)(F)F)cc2Br)c1F] | 100 | 60 | 16.67 | 0 |
| 1-7 | 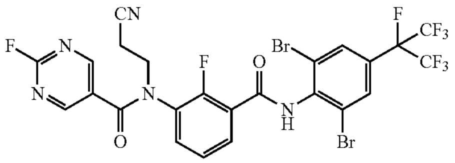 [SMILES: N#CCCN(C(=O)c1cnc(F)nc1)c1cccc(C(=O)Nc2c(Br)cc(C(F)(C(F)(F)F)C(F)(F)F)cc2Br)c1F] | 100 | 73.33 | 20 | 0 |
| 10 | 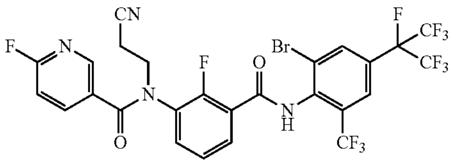 [SMILES: N#CCCN(C(=O)c1ccc(F)nc1)c1cccc(C(=O)Nc2c(Br)cc(C(F)(C(F)(F)F)C(F)(F)F)cc2C(F)(F)F)c1F] | 100 | 100 | 100 | 100 |
| 26 | 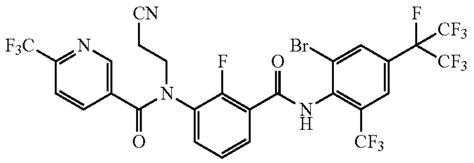 [SMILES: N#CCCN(C(=O)c1ccc(C(F)(F)F)nc1)c1cccc(C(=O)Nc2c(Br)cc(C(F)(C(F)(F)F)C(F)(F)F)cc2C(F)(F)F)c1F] | 100 | 100 | 96.67 | 73.33 |

TABLE 5-continued

Parallel comparison test of the insecticidal activity of the compounds 2, 10, 26 vs. the comparative compounds against *Plutella xylostella*

| Compound No. | Structural Formula | Lethality rate (%, 3 days after the treatment) 5 mg/L | 1 mg/L | 0.5 mg/L | 0.05 mg/L |
|---|---|---|---|---|---|
| 2-1 | 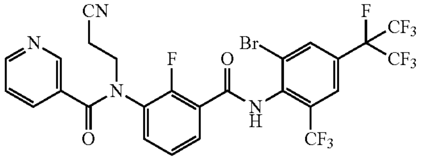 [SMILES: N#CCCN(C(=O)c1cccnc1)c1cccc(C(=O)Nc2c(Br)cc(C(F)(C(F)(F)F)C(F)(F)F)cc2C(F)(F)F)c1F] | 100 | 60 | 20 | 0 |
| 2-2 | 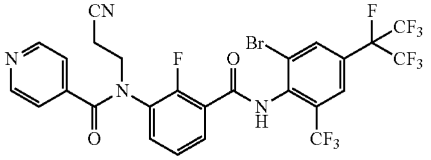 [SMILES: N#CCCN(C(=O)c1ccncc1)c1cccc(C(=O)Nc2c(Br)cc(C(F)(C(F)(F)F)C(F)(F)F)cc2C(F)(F)F)c1F] | 100 | 93.33 | 30 | 0 |
| 2-3 | 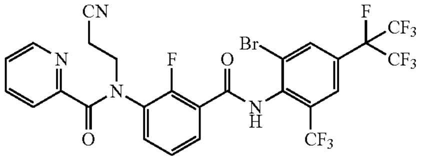 [SMILES: N#CCCN(C(=O)c1ccccn1)c1cccc(C(=O)Nc2c(Br)cc(C(F)(C(F)(F)F)C(F)(F)F)cc2C(F)(F)F)c1F] | 100 | 40 | 10 | 0 |
| 2-4 | 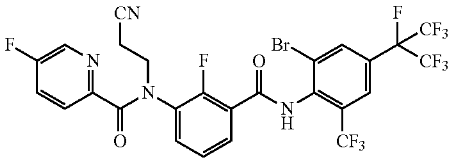 [SMILES: N#CCCN(C(=O)c1ccc(F)cn1)c1cccc(C(=O)Nc2c(Br)cc(C(F)(C(F)(F)F)C(F)(F)F)cc2C(F)(F)F)c1F] | 100 | 90 | 63.33 | 33.33 |
| 2-5 | 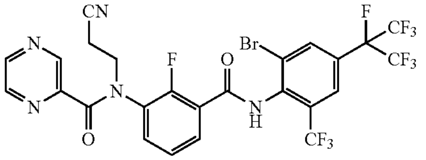 [SMILES: N#CCCN(C(=O)c1cnccn1)c1cccc(C(=O)Nc2c(Br)cc(C(F)(C(F)(F)F)C(F)(F)F)cc2C(F)(F)F)c1F] | 100 | 50 | 23.33 | 0 |
| 2-6 | 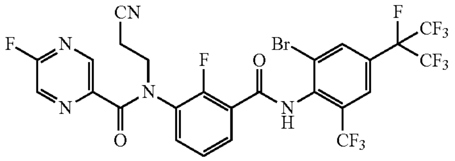 [SMILES: N#CCCN(C(=O)c1cnc(F)cn1)c1cccc(C(=O)Nc2c(Br)cc(C(F)(C(F)(F)F)C(F)(F)F)cc2C(F)(F)F)c1F] | 100 | 90 | 60 | 20 |
| 2-7 | 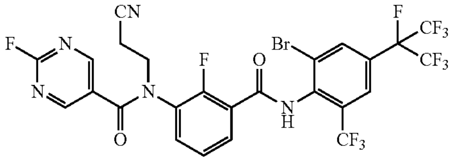 [SMILES: N#CCCN(C(=O)c1cnc(F)nc1)c1cccc(C(=O)Nc2c(Br)cc(C(F)(C(F)(F)F)C(F)(F)F)cc2C(F)(F)F)c1F] | 100 | 96.67 | 53.33 | 0 |

Note:

"—" in the table means untested, which applies also to the followings. In the table, 1-1, 1-2, 1-3, 1-4, 1-5, 1-6, 1-7, 2-1, 2-2, 2-3, 2-4, 2-5, 2-6, 2-7, and CKI were all comparative compounds provided in this application. These comparative compounds may be obtained by referring to the methods of Examples 15-35 of this disclosure, and the starting materials may be prepared according to examples herein, or may be commercial available, or may be prepared according to conventional methods.

In the embodiments of this disclosure, by selecting the groups $R_1$, $R_2$, $R_3$, $R_4$, $R_5$ in the compound of formula I and combinations thereof, compounds with better insecticidal effects may be obtained. As shown in Table 5, by comparing the compound 2 with the comparative compounds 1-1, 1-2, 1-3, 1-4, 1-5, CK1, 1-6, 1-7, and by comparing the compounds 10, 26 with the comparative compounds 2-1, 2-2, 2-3, 2-4, 2-5, 2-6, 2-7, it may be seen that: only when $R_5$ is F or $CF_3$, if and only when the ring connected to $R_5$ is the ring in this application, the corresponding compound (that is, the compound of general formula I) may exhibit a remarkably excellent insecticidal effect.

(3) Determination of the Insecticidal Activity Against *Chilo suppressalis*

Determination method: 1) Preparation of *Oryza sativa* seedlings: *Oryza sativa* was cultivated in a constant temperature room (a temperature of 26-28V, a relative humidity of about 60-80%, and a light illumination of 16 hL:8 hD) in a small plastic cup with a diameter of 4.5 cm and a height of 4 cm, and when the *Oryza sativa* grew up to the 4-5 leaf stage, robust and consistent *Oryza sativa* seedlings were selected for chemical treatment, and 3 repetitions were performed for each treatment. 2) Preparation for test insects: *Chilo suppressalis* at 3rd instar larvae were raised continuously indoors. 3) The *Oryza sativa* stems were sprayed and insects were introduced. Spraying was performed uniformly on the whole plant of the *Oryza sativa* seedlings, with 15 ml of compound solution for each treatment. The blank control was treated first, and then the above operations were repeated in the order of the test concentration from low to high. After the *Oryza sativa* seedlings were sprayed, they were placed in a cool place to dry the liquid, and about 5 cm of stalks at the base of the stems were cut and fed to the test insects. A glass petri dish with a diameter of 90 mm was placed with filter paper at the bottom of the dish, and then was moisturized by adding water. After that, about 5 rice stalks and 10 larvae were placed in each dish, and the petri dish was sealed with a non-woven fabric and placed in a constant temperature room for cultivation. The number of remaining live insects was investigated 3 days after the treatment.

Some of the determination results on the *Chilo suppressalis* were as follows:

At a dose of 1 mg/L, the lethality rates of compounds 1, 2, 3, 4, 5, 6, 9, 10, 11, 12, 13, 14, 15, 16, 17, 25, 26, 27, 28, 29, and 32 against *Chilo suppressalis* were 90% or more.

At a dose of 0.5 mg/L, the lethality rates of compounds 9, 10, 11, 12, 13, 14, 15, 16, 25, 26, 27, 28, 29, and 32 against *Chilo suppressalis* were 90% or more.

At a dose of 0.25 mg/L, the lethality rates of compounds 9, 10, 11, 12, 13, 14, 15, 16, 25, 26, 29 against *Chilo suppressalis* were 90% or more.

The compounds 2, 10 of this disclosure and the comparative compounds were selected for a parallel comparison test of the insecticidal activity against *Chilo suppressalis* (3 days after the treatment), through a same determination method as that described above. The results were shown in Table 6:

TABLE 6

Parallel comparison test of the insecticidal activity of the compounds 2, 10 vs. the comparative compounds against *Chilo suppressalis*

| | | Lethality rate (%, 3 days after the treatment) | | |
|---|---|---|---|---|
| Compound No. | Structural Formula | 10 mg/L | 1 mg/L | 0.5 mg/L |
| 2 | 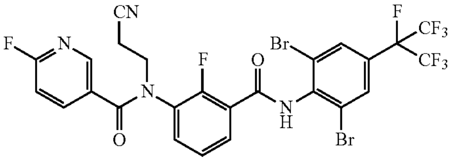 [SMILES: N#CCCN(C(=O)c1ccc(F)nc1)c1cccc(C(=O)Nc2c(Br)cc(C(F)(C(F)(F)F)C(F)(F)F)cc2Br)c1F] | 100 | 100 | 86.67 |
| 1-2 | 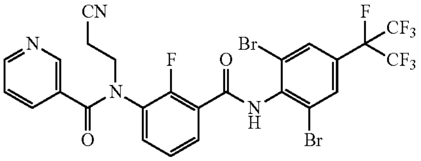 [SMILES: N#CCCN(C(=O)c1cccnc1)c1cccc(C(=O)Nc2c(Br)cc(C(F)(C(F)(F)F)C(F)(F)F)cc2Br)c1F] | 0 | 0 | — |
| CK1 | 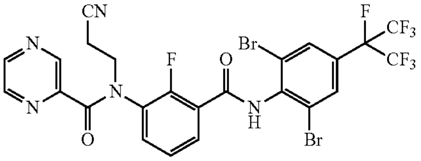 [SMILES: N#CCCN(C(=O)c1cnccn1)c1cccc(C(=O)Nc2c(Br)cc(C(F)(C(F)(F)F)C(F)(F)F)cc2Br)c1F] | 13.33 | 0 | — |
| 10 | 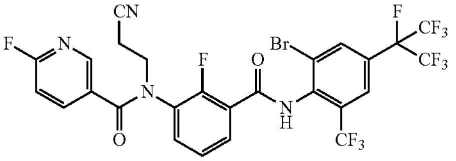 [SMILES: N#CCCN(C(=O)c1ccc(F)nc1)c1cccc(C(=O)Nc2c(Br)cc(C(F)(C(F)(F)F)C(F)(F)F)cc2C(F)(F)F)c1F] | 100 | 100 | 100 |

TABLE 6-continued

Parallel comparison test of the insecticidal activity of the compounds 2, 10 vs. the comparative compounds against *Chilo suppressalis*

| Compound No. | Structural Formula | Lethality rate (%, 3 days after the treatment) 10 mg/L | 1 mg/L | 0.5 mg/L |
|---|---|---|---|---|
| 2-5 | 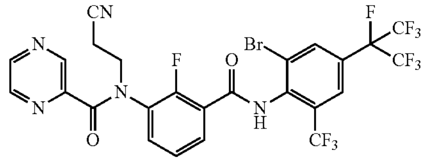 [SMILES: N#CCCN(C(=O)c1cnccn1)c1cccc(C(=O)Nc2c(Br)cc(C(F)(C(F)(F)F)C(F)(F)F)cc2C(F)(F)F)c1F] | 70 | 23.33 | 0 |

In the embodiments of this disclosure, by selecting the groups $R_1$, $R_2$, $R_3$, $R_4$, $R_5$ in the compound of formula I, compounds with better insecticidal effects may be obtained. As shown in Table 6, by comparing the compound 2 with the comparative compounds 1-2, CK1, and by comparing the compound 10 with the comparative compound 2-5, it may be seen that: only when $R_5$ is F or $CF_3$, if and only when the ring connected to $R_5$ is the ring in this application, the corresponding compound (that is, the compound of general formula I) may exhibit a remarkably excellent insecticidal effect. Furthermore, the compound of this disclosure also has very good insecticidal activity at a lower dosage.

Example 37: Insecticidal Test on Cat Fleas 4 mg of the test compound was dissolved in 40 ml of acetone to obtain an acetone solution with a concentration of 100 ppm. 400 μl of the compound solution was applied on the bottom and sides of a petri dish with an inner diameter of 5.3 cm, and then after the acetone was volatilized, a film of the compound of this disclosure was prepared on the inner wall of the petri dish. The petri dish used had an inner wall with an area of 40 $cm^2$, and a treatment dose of 1 $\mu g/cm^2$. It was then placed with 10 adult cat fleas (mixed male and female) therein, and after covered by the lid, it was stored in a constant temperature room at 25° C. The number of dead insects was checked after 72 h and the dead insect rate was calculated. The test was repeated 3 times. Test results: The compounds 1, 2, 3, 4, 5, 6, 9, 10, 11, 12, 13, 14, 15, 16, 17, 25, 26, 27, 28, 29, 32 showed over 90% of mortality rate of the insects.

Example 38: Insecticidal Test on American Dog Ticks 4 mg of the test compound was dissolved in 40 ml of acetone to obtain an acetone solution with a concentration of 100 ppm. 400 μl of the compound solution was applied on the bottom and sides of 2 petri dishes with an inner diameter of 5.3 cm, and then after the acetone was volatilized, a film of the compound of this disclosure was prepared on the inner wall of the petri dish. The petri dish used had an inner wall with an area of 40 $cm^2$, and a treatment dose of 1 $\mu g/cm^2$. It was then placed with 10 first nymphs of American dog ticks (mixed male and female) therein. After that, the 2 dishes were combined with an adhesive tape applied at the joint to prevent escaping of the insects, which was then stored in a constant temperature room at 25° C. The number of dead insects was checked after 24 h and the dead insect rate was calculated. The test was repeated 3 times. Test results: The compounds 1, 2, 3, 4, 5, 6, 9, 10, 11, 12, 13, 14, 15, 16, 17, 25, 26, 27, 28, 29, 32 showed over 90% of mortality rate of the insects.

INDUSTRIAL APPLICABILITY

This disclosure provides an isophthalamide compound with an excellent insecticidal activity. It may be used to prepare drugs for preventing and controlling pests in agriculture and other fields, and for preparing drugs for controlling animal parasites in the field of veterinary medicine.

The invention claimed is:

1. An isophthalamide compound, wherein the isophthalamide compound has a structure shown by formula I:

Formula I

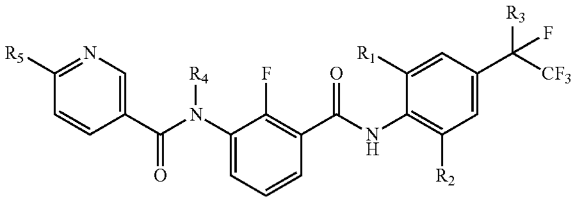

In the formula I:

$R_1$ is selected from halogen;

$R_2$ is selected from halogen, $C_1$-$C_4$ halogenoalkyl, and $C_1$-$C_4$ halogenoalkoxy;

$R_3$ is $CF_3$ or $CF_2CF_3$;

$R_4$ is selected from cyano $C_1$-$C_4$ alkyl;

$R_5$ is selected from fluorine, difluoromethyl, and trifluoromethyl.

2. The compound according to claim 1, wherein, in the formula I $R_1$ is bromine or iodine;

$R_2$ is selected from bromine, iodine, trifluoromethyl, and difluoromethoxy;

$R_3$ is $CF_3$ or $CF_2CF_3$;

$R_4$ is selected from $CH_2CN$, $CH_2CH_2CN$, $CH_2CH_2CH_2CN$, $CH_2CH_2CH_2CH_2CN$, $CH(CH_3)CN$, $CH(CH_2CH_3)CN$, $CH(CH_2CH_2CH_3)CN$, $C(CH_3)(CH_3)CN$, and $C(CH_3)(CH_2CH_3)CN$;

$R_5$ is selected from fluorine, difluoromethyl, and trifluoromethyl.

3. The isophthalamide compound according to claim 1, wherein the isophthalamide compound is selected from:

compounds in Table 1, wherein the compounds in Table 1 have a structure shown by the formula I and $R_1$, $R_2$, $R_3$, $R_4$, and $R_5$ are as shown in Table 1:

TABLE 1

| Compound No. | $R_1$ | $R_2$ | $R_3$ | $R_4$ | $R_5$ |
|---|---|---|---|---|---|
| 1 | Br | Br | $CF_3$ | $CH_2CN$ | F |
| 2 | Br | Br | $CF_3$ | $CH_2CH_2CN$ | F |
| 3 | Br | Br | $CF_3$ | $CH_2CH_2CH_2CN$ | F |
| 4 | Br | Br | $CF_3$ | $CH_2CH_2CH_2CH_2CN$ | F |
| 5 | Br | I | $CF_3$ | $CH_2CN$ | F |
| 6 | Br | I | $CF_3$ | $CH_2CH_2CN$ | F |
| 7 | Br | I | $CF_3$ | $CH_2CH_2CH_2CN$ | F |
| 8 | Br | I | $CF_3$ | $CH_2CH_2CH_2CH_2CN$ | F |
| 9 | Br | $CF_3$ | $CF_3$ | $CH_2CN$ | F |
| 10 | Br | $CF_3$ | $CF_3$ | $CH_2CH_2CN$ | F |
| 11 | Br | $CF_3$ | $CF_3$ | $CH_2CH_2CH_2CN$ | F |
| 12 | Br | $CF_3$ | $CF_3$ | $CH_2CH_2CH_2CH_2CN$ | F |
| 13 | I | $CF_3$ | $CF_3$ | $CH_2CN$ | F |
| 14 | I | $CF_3$ | $CF_3$ | $CH_2CH_2CN$ | F |
| 15 | I | $CF_3$ | $CF_3$ | $CH_2CH_2CH_2CN$ | F |
| 16 | I | $CF_3$ | $CF_3$ | $CH_2CH_2CH_2CH_2CN$ | F |
| 17 | Br | Br | $CF_3$ | $CH_2CN$ | $CF_3$ |
| 18 | Br | Br | $CF_3$ | $CH_2CH_2CN$ | $CF_3$ |
| 19 | Br | Br | $CF_3$ | $CH_2CH_2CH_2CN$ | $CF_3$ |
| 20 | Br | Br | $CF_3$ | $CH_2CH_2CH_2CH_2CN$ | $CF_3$ |
| 21 | Br | I | $CF_3$ | $CH_2CN$ | $CF_3$ |
| 22 | Br | I | $CF_3$ | $CH_2CH_2CN$ | $CF_3$ |
| 23 | Br | I | $CF_3$ | $CH_2CH_2CH_2CN$ | $CF_3$ |
| 24 | Br | I | $CF_3$ | $CH_2CH_2CH_2CH_2CN$ | $CF_3$ |
| 25 | Br | $CF_3$ | $CF_3$ | $CH_2CN$ | $CF_3$ |
| 26 | Br | $CF_3$ | $CF_3$ | $CH_2CH_2CN$ | $CF_3$ |
| 27 | Br | $CF_3$ | $CF_3$ | $CH_2CH_2CH_2CN$ | $CF_3$ |
| 28 | Br | $CF_3$ | $CF_3$ | $CH_2CH_2CH_2CH_2CN$ | $CF_3$ |
| 29 | I | $CF_3$ | $CF_3$ | $CH_2CN$ | $CF_3$ |
| 30 | I | $CF_3$ | $CF_3$ | $CH_2CH_2CN$ | $CF_3$ |
| 31 | I | $CF_3$ | $CF_3$ | $CH_2CH_2CH_2CN$ | $CF_3$ |
| 32 | I | $CF_3$ | $CF_3$ | $CH_2CH_2CH_2CH_2CN$ | $CF_3$ |
| 33 | Br | Br | $CF_3$ | $CH_2CN$ | $CHF_2$ |
| 34 | Br | Br | $CF_3$ | $CH_2CH_2CN$ | $CHF_2$ |
| 35 | Br | Br | $CF_3$ | $CH_2CH_2CH_2CN$ | $CHF_2$ |
| 36 | Br | Br | $CF_3$ | $CH_2CH_2CH_2CH_2CN$ | $CHF_2$ |
| 37 | Br | I | $CF_3$ | $CH_2CN$ | $CHF_2$ |
| 38 | Br | I | $CF_3$ | $CH_2CH_2CN$ | $CHF_2$ |
| 39 | Br | I | $CF_3$ | $CH_2CH_2CH_2CN$ | $CHF_2$ |
| 40 | Br | I | $CF_3$ | $CH_2CH_2CH_2CH_2CN$ | $CHF_2$ |
| 41 | Br | $CF_3$ | $CF_3$ | $CH_2CN$ | $CHF_2$ |
| 42 | Br | $CF_3$ | $CF_3$ | $CH_2CH_2CN$ | $CHF_2$ |
| 43 | Br | $CF_3$ | $CF_3$ | $CH_2CH_2CH_2CN$ | $CHF_2$ |
| 44 | Br | $CF_3$ | $CF_3$ | $CH_2CH_2CH_2CH_2CN$ | $CHF_2$ |
| 45 | I | $CF_3$ | $CF_3$ | $CH_2CN$ | $CHF_2$ |
| 46 | I | $CF_3$ | $CF_3$ | $CH_2CH_2CN$ | $CHF_2$ |
| 47 | I | $CF_3$ | $CF_3$ | $CH_2CH_2CH_2CN$ | $CHF_2$ |
| 48 | I | $CF_3$ | $CF_3$ | $CH_2CH_2CH_2CH_2CN$ | $CHF_2$ |
| 49 | Br | Br | $CF_2CF_3$ | $CH_2CN$ | F |
| 50 | Br | Br | $CF_2CF_3$ | $CH_2CH_2CN$ | F |
| 51 | Br | Br | $CF_2CF_3$ | $CH_2CH_2CH_2CN$ | F |
| 52 | Br | Br | $CF_2CF_3$ | $CH_2CH_2CH_2CH_2CN$ | F |
| 53 | Br | I | $CF_2CF_3$ | $CH_2CN$ | F |
| 54 | Br | I | $CF_2CF_3$ | $CH_2CH_2CN$ | F |
| 55 | Br | I | $CF_2CF_3$ | $CH_2CH_2CH_2CN$ | F |
| 56 | Br | I | $CF_2CF_3$ | $CH_2CH_2CH_2CH_2CN$ | F |
| 57 | Br | $CF_3$ | $CF_2CF_3$ | $CH_2CN$ | F |
| 58 | Br | $CF_3$ | $CF_2CF_3$ | $CH_2CH_2CN$ | F |
| 59 | Br | $CF_3$ | $CF_2CF_3$ | $CH_2CH_2CH_2CN$ | F |
| 60 | Br | $CF_3$ | $CF_2CF_3$ | $CH_2CH_2CH_2CH_2CN$ | F |
| 61 | I | $CF_3$ | $CF_2CF_3$ | $CH_2CN$ | F |
| 62 | I | $CF_3$ | $CF_2CF_3$ | $CH_2CH_2CN$ | F |
| 63 | I | $CF_3$ | $CF_2CF_3$ | $CH_2CH_2CH_2CN$ | F |
| 64 | I | $CF_3$ | $CF_2CF_3$ | $CH_2CH_2CH_2CH_2CN$ | F |
| 65 | Br | Br | $CF_2CF_3$ | $CH_2CN$ | $CF_3$ |
| 66 | Br | Br | $CF_2CF_3$ | $CH_2CH_2CN$ | $CF_3$ |
| 67 | Br | Br | $CF_2CF_3$ | $CH_2CH_2CH_2CN$ | $CF_3$ |
| 68 | Br | Br | $CF_2CF_3$ | $CH_2CH_2CH_2CH_2CN$ | $CF_3$ |
| 69 | Br | I | $CF_2CF_3$ | $CH_2CN$ | $CF_3$ |
| 70 | Br | I | $CF_2CF_3$ | $CH_2CH_2CN$ | $CF_3$ |
| 71 | Br | I | $CF_2CF_3$ | $CH_2CH_2CH_2CN$ | $CF_3$ |
| 72 | Br | I | $CF_2CF_3$ | $CH_2CH_2CH_2CH_2CN$ | $CF_3$ |
| 73 | Br | $CF_3$ | $CF_2CF_3$ | $CH_2CN$ | $CF_3$ |
| 74 | Br | $CF_3$ | $CF_2CF_3$ | $CH_2CH_2CN$ | $CF_3$ |
| 75 | Br | $CF_3$ | $CF_2CF_3$ | $CH_2CH_2CH_2CN$ | $CF_3$ |
| 76 | Br | $CF_3$ | $CF_2CF_3$ | $CH_2CH_2CH_2CH_2CN$ | $CF_3$ |
| 77 | I | $CF_3$ | $CF_2CF_3$ | $CH_2CN$ | $CF_3$ |
| 78 | I | $CF_3$ | $CF_2CF_3$ | $CH_2CH_2CN$ | $CF_3$ |
| 79 | I | $CF_3$ | $CF_2CF_3$ | $CH_2CH_2CH_2CN$ | $CF_3$ |
| 80 | I | $CF_3$ | $CF_2CF_3$ | $CH_2CH_2CH_2CH_2CN$ | $CF_3$ |
| 81 | Br | Br | $CF_2CF_3$ | $CH_2CN$ | $CHF_2$ |
| 82 | Br | Br | $CF_2CF_3$ | $CH_2CH_2CN$ | $CHF_2$ |
| 83 | Br | Br | $CF_2CF_3$ | $CH_2CH_2CH_2CN$ | $CHF_2$ |
| 84 | Br | Br | $CF_2CF_3$ | $CH_2CH_2CH_2CH_2CN$ | $CHF_2$ |
| 85 | Br | I | $CF_2CF_3$ | $CH_2CN$ | $CHF_2$ |
| 86 | Br | I | $CF_2CF_3$ | $CH_2CH_2CN$ | $CHF_2$ |
| 87 | Br | I | $CF_2CF_3$ | $CH_2CH_2CH_2CN$ | $CHF_2$ |
| 88 | Br | I | $CF_2CF_3$ | $CH_2CH_2CH_2CH_2CN$ | $CHF_2$ |
| 89 | Br | $CF_3$ | $CF_2CF_3$ | $CH_2CN$ | $CHF_2$ |
| 90 | Br | $CF_3$ | $CF_2CF_3$ | $CH_2CH_2CN$ | $CHF_2$ |
| 91 | Br | $CF_3$ | $CF_2CF_3$ | $CH_2CH_2CH_2CN$ | $CHF_2$ |
| 92 | Br | $CF_3$ | $CF_2CF_3$ | $CH_2CH_2CH_2CH_2CN$ | $CHF_2$ |
| 93 | I | $CF_3$ | $CF_2CF_3$ | $CH_2CN$ | $CHF_2$ |
| 94 | I | $CF_3$ | $CF_2CF_3$ | $CH_2CH_2CN$ | $CHF_2$ |
| 95 | I | $CF_3$ | $CF_2CF_3$ | $CH_2CH_2CH_2CN$ | $CHF_2$ |
| 96 | I | $CF_3$ | $CF_2CF_3$ | $CH_2CH_2CH_2CH_2CN$ | $CHF_2$. |

4. The isophthalamide compound according to claim 1, wherein the isophthalamide compound is selected from:

compounds in Table 2, wherein the compounds in Table 2 have a structure shown by the formula I and $R_1$, $R_2$, $R_3$, $R_4$ and $R_5$ are as shown in Table 2:

TABLE 2

| Compound No. | $R_1$ | $R_2$ | $R_3$ | $R_4$ | $R_5$ |
|---|---|---|---|---|---|
| 1 | Br | Br | $CF_3$ | $CH_2CN$ | F |
| 2 | Br | Br | $CF_3$ | $CH_2CH_2CN$ | F |
| 3 | Br | Br | $CF_3$ | $CH_2CH_2CH_2CN$ | F |
| 4 | Br | Br | $CF_3$ | $CH_2CH_2CH_2CH_2CN$ | F |
| 5 | Br | I | $CF_3$ | $CH_2CN$ | F |
| 6 | Br | I | $CF_3$ | $CH_2CH_2CN$ | F |
| 7 | Br | I | $CF_3$ | $CH_2CH_2CH_2CN$ | F |
| 8 | Br | I | $CF_3$ | $CH_2CH_2CH_2CH_2CN$ | F |
| 9 | Br | $CF_3$ | $CF_3$ | $CH_2CN$ | F |
| 10 | Br | $CF_3$ | $CF_3$ | $CH_2CH_2CN$ | F |
| 11 | Br | $CF_3$ | $CF_3$ | $CH_2CH_2CH_2CN$ | F |
| 12 | Br | $CF_3$ | $CF_3$ | $CH_2CH_2CH_2CH_2CN$ | F |
| 13 | I | $CF_3$ | $CF_3$ | $CH_2CN$ | F |
| 14 | I | $CF_3$ | $CF_3$ | $CH_2CH_2CN$ | F |
| 15 | I | $CF_3$ | $CF_3$ | $CH_2CH_2CH_2CN$ | F |
| 16 | I | $CF_3$ | $CF_3$ | $CH_2CH_2CH_2CH_2CN$ | F |
| 17 | Br | Br | $CF_3$ | $CH_2CN$ | $CF_3$ |
| 18 | Br | Br | $CF_3$ | $CH_2CH_2CN$ | $CF_3$ |
| 19 | Br | Br | $CF_3$ | $CH_2CH_2CH_2CN$ | $CF_3$ |
| 20 | Br | Br | $CF_3$ | $CH_2CH_2CH_2CH_2CN$ | $CF_3$ |
| 21 | Br | I | $CF_3$ | $CH_2CN$ | $CF_3$ |
| 22 | Br | I | $CF_3$ | $CH_2CH_2CN$ | $CF_3$ |
| 23 | Br | I | $CF_3$ | $CH_2CH_2CH_2CN$ | $CF_3$ |
| 24 | Br | I | $CF_3$ | $CH_2CH_2CH_2CH_2CN$ | $CF_3$ |
| 25 | Br | $CF_3$ | $CF_3$ | $CH_2CN$ | $CF_3$ |
| 26 | Br | $CF_3$ | $CF_3$ | $CH_2CH_2CN$ | $CF_3$ |
| 27 | Br | $CF_3$ | $CF_3$ | $CH_2CH_2CH_2CN$ | $CF_3$ |
| 28 | Br | $CF_3$ | $CF_3$ | $CH_2CH_2CH_2CH_2CN$ | $CF_3$ |
| 29 | I | $CF_3$ | $CF_3$ | $CH_2CN$ | $CF_3$ |
| 30 | I | $CF_3$ | $CF_3$ | $CH_2CH_2CN$ | $CF_3$ |
| 31 | I | $CF_3$ | $CF_3$ | $CH_2CH_2CH_2CN$ | $CF_3$ |
| 32 | I | $CF_3$ | $CF_3$ | $CH_2CH_2CH_2CH_2CN$ | $CF_3$. |

5. An insecticide formulation, wherein the insecticide formulation comprises the isophthalamide compound according to claim 1 as an active component, and also one or more adjuvants; and optionally, the amount of the isophthalamide compound according to claim 1 in the insecticide formulation is 0.1% to 99% by weight, further optionally, 0.5% to 90% by weight.

6. An insecticide composition, comprising a mixture of the isophthalamide compound according to claim 1 and another active compound, wherein the another active compound is one or more selected from an insecticide, a poison bait, a disinfectant, an acaricide, a nematicide, a fungicide, a growth regulator, and a herbicide.

7. A method for controlling an agricultural or forestry pest, comprising applying an effective dose of a material to the pest to be controlled or a growth medium thereof, wherein the material is one or more selected from the following group:

the isophthalamide compound according to claim 1;
the insecticide formulation; and
the insecticide composition.

8. An animal parasite control agent, comprising the isophthalamide compound according to claim 1 as an active component, and also one or more adjuvants; and optionally, the amount of the isophthalamide compound according to claim 1 in the animal parasite control agent is 1% to 80% by weight.

9. An animal parasite control composition, comprising a mixture of the isophthalamide compound according to claim 1 and another active animal parasite control compound, wherein the another active animal parasite control compound is one or more selected from an acaricide, an insecticide, a parasiticide, and antimalarial agent.

10. A method for controlling an animal parasite, comprising the step of applying an effective dose of a material to the animal parasite to be controlled or a growth medium thereof, wherein the material is one or more selected from the following group:

the isophthalamide according to claim 1;
the animal parasite control agent; and
the animal parasite control composition.

* * * * *